(12) United States Patent
Dugenet et al.

(10) Patent No.: US 9,364,538 B2
(45) Date of Patent: Jun. 14, 2016

(54) COMPOSITIONS CONTAINING MIXTURES OF FERMENTABLE FIBERS

(75) Inventors: Yann Dugenet, Sait-Brieuc (FR); Heidi Jacobs, Zingem (BE); Christian Fougnies, Warcoing (BE); Beatrice Morio, Saint-Georges-sur-Allier (FR); Veronique Coxam, Ceyrat (FR); Annick Bernalier, La Roche Blanche (FR)

(73) Assignee: COSUCRA-GROUPE WARCOING SA, Warcoing (BE)

( * ) Notice: Subject to any disclaimer, the term of this patent is extended or adjusted under 35 U.S.C. 154(b) by 501 days.

(21) Appl. No.: 13/389,061

(22) PCT Filed: Aug. 18, 2010

(86) PCT No.: PCT/EP2010/062039
§ 371 (c)(1),
(2), (4) Date: Feb. 6, 2012

(87) PCT Pub. No.: WO2011/020853
PCT Pub. Date: Feb. 24, 2011

(65) Prior Publication Data
US 2012/0135957 A1 May 31, 2012

(30) Foreign Application Priority Data
Aug. 18, 2009 (EP) .................................... 09290632

(51) Int. Cl.
| | | |
|---|---|---|
| *A61K 31/733* | (2006.01) | |
| *A61P 29/00* | (2006.01) | |
| *A61K 45/06* | (2006.01) | |
| *A23L 1/0528* | (2006.01) | |
| *A23L 1/30* | (2006.01) | |
| *A23L 1/308* | (2006.01) | |
| *A61K 31/702* | (2006.01) | |
| *A61K 31/715* | (2006.01) | |
| *A61K 31/716* | (2006.01) | |

(52) U.S. Cl.
CPC ............... *A61K 45/06* (2013.01); *A23L 1/0528* (2013.01); *A23L 1/3002* (2013.01); *A23L 1/3081* (2013.01); *A61K 31/702* (2013.01); *A61K 31/715* (2013.01); *A61K 31/716* (2013.01); *A23V 2002/00* (2013.01)

(58) Field of Classification Search
CPC ... A23L 1/0528; A23L 1/3002; A23L 1/3081; A61K 31/702; A61K 31/715; A61K 31/716; A61K 2300/00; A23V 2002/00; A23V 2250/5062; A23V 2250/51088; A23V 2250/54246; A23V 2250/628; A23V 2250/18; A23V 2250/1882; A23V 2250/70; A23V 2250/156; A23V 2250/5118; A23V 2200/332; A23V 2200/328
USPC ............................................................ 514/54
See application file for complete search history.

(56) References Cited

U.S. PATENT DOCUMENTS

2008/0031814 A1 * 2/2008 Hageman ....................... 424/9.1

FOREIGN PATENT DOCUMENTS

| WO | WO99/61036 | * 12/1999 | ............. A61K 35/78 |
|---|---|---|---|
| WO | WO 99/61036 | 12/1999 | |
| WO | WO 02/08330 | 1/2002 | |
| WO | WO 2004/052121 | 6/2004 | |
| WO | WO 2005/077391 | 8/2005 | |
| WO | WO 2006/002495 | 1/2006 | |
| WO | WO 2008/087167 | 7/2008 | |
| WO | WO 2008/153377 | 12/2008 | |
| WO | WO 2008/153377 A1 * 12/2008 | | ................ A23L 1/30 |
| WO | WO 2010/081913 | 7/2010 | |

OTHER PUBLICATIONS

The Merck Manual, 16th Ed., 1999, pp. 183-89, 339-342 and 1488-1490.*
Izydorczyk et al, Carbohydrate Polymers, 1995, 28, 33-48.*
The Merck Manual, 1992, p. 411.*
Wisse, B. E. , J. Am. Soc. Nephrol, 2004, 15, 2792-2800.*
Dinarello, C.A., Chest, 2000, 118(2), 503-508.*
Hsu, et al. "Xylooligosaccharides and Fructooligosaccharides Affect the Intestinal Microbiota and Precancerous Colonic Lesion Development in Rats," *The Journal of Nutrition*, vol. 134, No. 6, pp. 1523-1528, Jun. 1, 2004.
International Search Report dated Dec. 10, 2010 issued to international application No. PCT/EP2010/062039.

* cited by examiner

*Primary Examiner* — Ganapathy Krishnan
(74) *Attorney, Agent, or Firm* — Knobbe, Martens, Olson & Bear, LLP

(57) ABSTRACT

The present invention relates to synergistic compositions comprising mixtures of fermentable fibers. The present invention specifically relates to composition comprising inulin and arabinoxylan for use in reducing, preventing and/or treating inflammation, wherein said arabinoxylan is partially hydrolyzed arabinoxylan and wherein the ratio of said inulin to said arabinoxylan and/or partially hydrolyzed arabinoxylan is between 65%/35% by weight and 90%/10% by weight.

7 Claims, 12 Drawing Sheets

COMPOSITIONS CONTAINING MIXTURES OF FERMENTABLE FIBERS

CROSS-REFERENCE TO RELATED APPLICATIONS

This application is the U.S. National Phase under 35 U.S.C. §371 of International Application PCT/EP2010/062039, filed Aug. 18, 2010, which claims priority to EP Application No. 09290632.0, filed Aug. 18, 2009.

FIELD OF THE INVENTION

The present invention relates to compositions comprising fermentable fibers for preventing, reducing and/or treating inflammation. More in particular, the present invention relates to synergistic combinations of linear and branched fermentable fibers for modulating the inflammatory response of animals and humans following an immune challenge.

BACKGROUND OF THE INVENTION

Inflammation is a complex biological response to harmful stimuli, such as pathogens, damaged cells, or irritants. The inflammatory response is an attempt by the body to restore and maintain homeostasis after invasion by an infectious agent, antigen challenge, or physical, chemical or traumatic damage. Localized inflammation is contained in a specific region and can exhibit varying symptoms, including redness, swelling, heat and pain. While the inflammatory response is generally considered a healthy response to injury, the immune system can present an undesirable physiological response if it is not appropriately regulated. In this situation, the body's normally protective immune system causes damage to its own tissue by treating healthy tissue as if it is infected or abnormal. Alternatively, if there is an injury, the inflammatory response may be out of proportion with the threat causing the injury. When this occurs, the inflammatory response can cause more damage to the body than the agent itself would have produced.

The inflammatory response has been found in part to consist of an increased expression of both pro-inflammatory and anti-inflammatory cytokines. Cytokines are low molecular weight, biologically active proteins involved in the coordination of immunological and inflammatory responses and communication between specific immune cell populations. A number of cell types produce cytokines during inflammatory reactions, including neutrophils, monocytes, and lymphocytes. Multiple mechanisms exist by which cytokines generated at inflammatory sites influence the inflammatory response. If a proinflammatory response is not successfully countered by anti-inflammatory cytokines, however, uncontrolled systemic inflammation can occur. In contrast to localized inflammation, systemic inflammation is widespread throughout the body. This type of inflammation may include localized inflammation at specific sites, but may also be associated with general "flu-like" symptoms, including fever, chills, fatigue or loss of energy, headaches, loss of appetite, and muscle stiffness. Systemic inflammation can lead to protein degradation, catabolism and hypermetabolism. As a consequence, the structure and function of essential organs, such as muscle, heart, immune system and liver may be compromised and can contribute to multi-organ failure and mortality.

Although enormous progress has been achieved in understanding the mechanisms of systemic inflammation, the mortality rate due to this disorder remains unacceptably high.

There is therefore still a need to develop compositions having improved physiological and/or pharmacological and/or therapeutic activities for the prevention and/or treatment of inflammation. It is accordingly one of the objects of the present invention to overcome or ameliorate at least one of the disadvantages of the prior art, or to provide a useful alternative.

SUMMARY OF THE INVENTION

The present inventors surprisingly found that inulin and arabinoxylan in particular a combination of inulin and partially hydrolyzed arabinoxylan (AXOS) synergistically reduce, prevent and/or treat inflammation, in particular systemic inflammation.

Therefore the present invention concerns a composition comprising inulin and arabinoxylan for reducing, treating and/or preventing inflammation, in particular systemic inflammation. In particular the present invention concerns a composition comprising inulin and arabinoxylan for use in reducing, preventing and/or treating inflammation, wherein said arabinoxylan is partially hydrolyzed arabinoxylan and wherein the ratio of said inulin to said arabinoxylan and/or partially hydrolyzed arabinoxylan is between 65%/35% by weight and 90%/10% by weight.

The present inventors have found that the present composition synergistically attenuate at the same time the elevation of pro-inflammatory cytokines (such as TNF-α, IL-1β, IL-8, IL-12, IFN-γ) and the suppression of anti-inflammatory cytokines (such as IL-10, IL-4, IL-13), following harmful stimuli such as a challenge with lipopolysaccharide (LPS). The present composition comprising inulin and arabinoxylan or AXOS has therefore the advantage of improving resistance to stress, inflammation and/or immune challenge in humans and animals. The present invention therefore also concerns a composition comprising inulin and arabinoxylan and/or partially hydrolyzed arabinoxylan for attenuating at the same time the elevation (increase) of pro-inflammatory cytokines and the suppression of anti-inflammatory cytokines following a challenge with LPS. In particular the present invention also concerns a composition comprising inulin and arabinoxylan for use in attenuating at the same time the elevation (increase) of pro-inflammatory cytokines and the suppression of anti-inflammatory cytokines following a challenge with LPS, wherein said arabinoxylan is partially hydrolyzed arabinoxylan and wherein the ratio of said inulin to said arabinoxylan and/or partially hydrolyzed arabinoxylan is between 65%/35% by weight and 90%/10% by weight.

The present composition was also found to be able to reduce LPS concentration in the blood and therefore can be used to reduce LPS concentrations or levels in the blood. LPS can contribute to the initiation and development of inflammation, insulin-resistance and/or fat storage. Therefore the present invention offers great potential in the fight against obesity, metabolic syndrome and/or type-2 diabetes. Therefore, the present invention also concerns a composition comprising inulin and arabinoxylan and/or AXOS for preventing, treating and/or attenuating obesity, metabolic syndrome and/or type-2 diabetes. In particular, the present invention also concerns a composition comprising inulin and arabinoxylan and/or AXOS for use in preventing, treating and/or attenuating obesity, metabolic syndrome and/or type-2 diabetes, wherein said arabinoxylan is partially hydrolyzed arabinoxylan and wherein the ratio of said inulin to said arabinoxylan and/or partially hydrolyzed arabinoxylan is between 65%/35% by weight and 90%/10% by weight.

Another aspect of the invention also concerns a composition comprising inulin and arabinoxylan wherein the ratio inulin/arabinoxylan is ranging between 65%/35% by weight and 95%/5% by weight. In particular, the present invention also concerns a composition comprising inulin and arabinoxylan and/or partially hydrolyzed arabinoxylan, wherein the ratio of said inulin to said arabinoxylan and/or partially hydrolyzed arabinoxylan is between 65%/35% by weight and 90%/10% by weight. The present invention also concerns the use of said composition as a prebiotic.

The present invention also encompasses a food or beverage product or a food supplement comprising between 0.1 and 10 g of a composition according the present invention, per serving of the said food or beverage product or food supplement.

The present invention also contemplates the use of a composition according to the present invention as a food additive in the production of a food or beverage product or a food supplement, which comprises between 0.1 and 10 g of said composition per serving of the said food or beverage product or food supplement.

DESCRIPTION OF THE FIGURES

FIGS. 1A to 1E represent graphs plotting the effect of maltodextrin (placebo), AXOS and a mixture of 75% inulin and 25% AXOS according to embodiment of the invention on fermentation and inflammatory characteristics: wherein FIG. 1A shows the effect on the amounts of acetate, propionate and butyrate, expressed in μmol/g fecal dry matter, statistical differences between groups: * $p=0.01$, ** $p<0.001$; wherein FIG. 1B shows the effect on the fecal secretory IgA levels, expressed as μg/ml fecal water; wherein FIG. 1C shows the effect on the relative expression of pro-inflammatory cytokines, statistical differences between groups: * $p=0.045$; wherein FIG. 1D shows the effect on the relative expression of anti-inflammatory cytokines, statistical differences between groups: ** $p=0.01$: and wherein FIG. 1E shows the effect on the circulatory LPS, expressed as EU/ml, statistical differences between groups: $p=0.03$.

FIGS. 2A to 2E represent graphs plotting the effect of inulin, AXOS and varying compositions comprising inulin and AXOS according to embodiments of the invention on different in vitro fermentation characteristics: wherein FIG. 2A shows the effect on the half-time of asymptotic gas production (T/2), expressed in h; wherein FIG. 2B shows the effect on total SCFA, expressed as mM/g dry matter; wherein FIG. 2C shows the effect on acetate, expressed as mM/g dry matter; wherein FIG. 2D shows the effect on propionate, expressed as mM/g dry matter; and wherein FIG. 2E shows the effect on butyrate, expressed as mM/g dry matter. Statistical significant differences were indicated as follows: (*) $0.05<p<0.1$ versus inulin, * $p<0.05$ versus inulin, ** $p<0.01$ versus inulin, (&) $0.05<p<0.1$ versus AXOS, & $p<0.05$ versus AXOS, && $p<0.01$ versus AXOS.

FIGS. 4A to 4H represent graphs plotting the effects of inulin, AXOS and a mixture of 80% inulin and 20% AXOS according to the embodiment of the invention on inflammatory characteristics in an animal model: wherein FIG. 4A shows the effect on the weight evolution of the animals, expressed in g; wherein FIG. 4B shows the effect on final body weight of the animals, expressed in g; wherein FIG. 4C shows the effect on the sub-cutaneous adipose tissue weight, expressed in g/100 g total weight; wherein FIG. 4D shows the effect on the visceral adipose tissue weight, expressed in g/100 g total weight; wherein FIG. 4E shows the effect on the tibialis anterior weight, expressed in g/100 g total weight; wherein FIG. 4F shows the effect on the soleus weight, expressed in g/100 g total weight, wherein FIG. 4G shows the effect on the blood leptin level in a fasting state, expressed in ng/ml, wherein FIG. 4H shows the effect on high sensitivity C-reactive protein (hs-CRP) level, expressed in mg/l. In all of the FIGS. 4A to 4H, "SH" stands for sham-operated rats, "OVX" stands for ovariectomized rats, "basic" stands for basic diet, "test" stands for obesigenic test diet, "AXOS" stands for 7.5% AXOS preparation, "inulin" stands for 7.5% inulin preparation and "AXOS+inulin" stands for 5.625% inulin preparation and 1.875% AXOS preparation. Within each individual Figure, groups with the same letter are not significantly different (based on a statistical significance level of $p<0.05$).

DESCRIPTION OF THE INVENTION

Figure 1A:
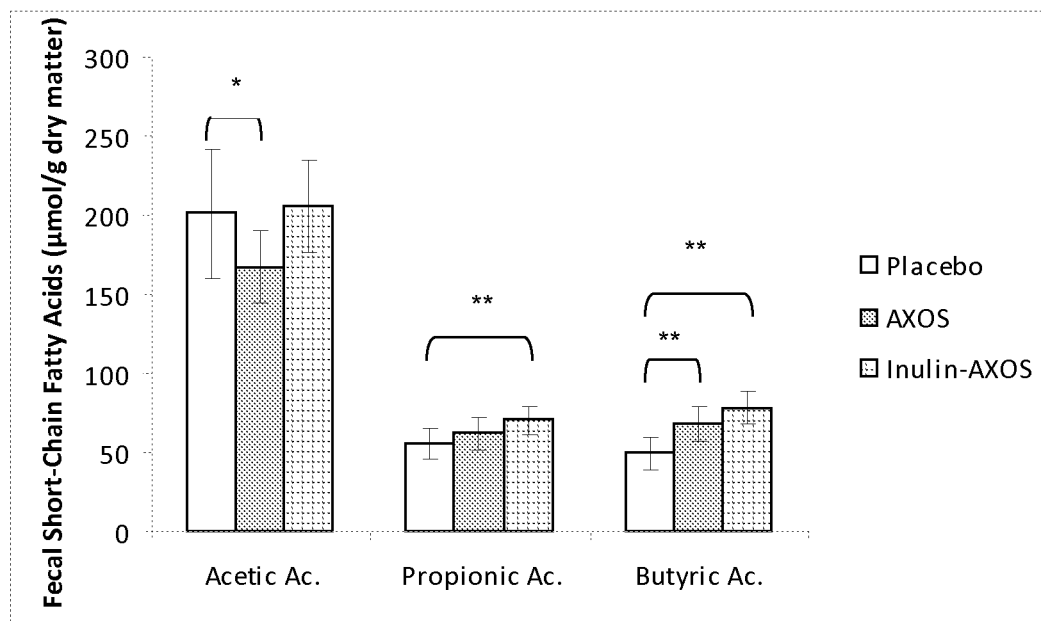

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Thus the present invention concerns a composition comprising inulin and arabinoxylan for reducing, preventing and/or treating inflammation. In one embodiment, said inflammation is systemic inflammation. The present invention preferably concerns a composition comprising inulin and arabinoxylan, wherein said arabinoxylan is partially hydrolyzed arabinoxylan and wherein the ratio of said inulin to said arabinoxylan and/or partially hydrolyzed arabinoxylan is between 65%/35% by weight and 90%/10% by weight, for use in reducing, preventing and/or treating inflammation.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

As used in the specification and the appended claims, the singular forms "a", "an," and "the" include plural referents unless the context clearly dictates otherwise. By way of example, "an arabinoxylan oligosaccharide" means one arabinoxylan oligosaccharide or more than one arabinoxylan oligosaccharide.

As used herein, the terms "about" and "approximately", when referring to a measurable value such as a parameter, an amount, a temporal duration, and the like, is meant to encompass variations of and from the specified value, in particular variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" or "approximately" refers is itself also specifically, and preferably, disclosed.

As used herein, the term "monosaccharide" refers to a single sugar unit which is the building block of oligo- and polysaccharides. Non-limiting examples of monosaccharide include glucose, fructose, xylose, arabinose, galactose, mannose and the like.

As used herein, the term "carbohydrate" refers to a polyhydroxy-aldehyde (aldose) or ketone (ketose) or to a substance which yields one or more of these substances by hydrolysis.

As used herein, the terms "degree of polymerization" or "(DP)" relates to the number of monosaccharide residues present in an oligo- or polysaccharide. Often also the parameter average degree of polymerization is used. The degree of polymerization is a measure of molecular weight (MW). The DP can be calculated as the ratio of the total MW of the polymer or oligomer and the MW of the repeating units.

The average degree of polymerization (av DP) of a (polydispersed) oligo- or polysaccharide mixture is the mean of the degree of polymerization (DP) of all the molecules present in this saccharide mixture. The average degree of polymerization can be calculated based on the number of molecules for each DP: av $DP_n$ (1) (or average degree of polymerization by number), or based on the weight of the molecules for each DP: av $DP_w$ (2). In the present patent application, unless otherwise specified, the average degree of polymerization is considered to be the av $DP_n$ and can be calculated as described herein.

(1) Average $DP_n$ can be determined as the total number of moles of monomers after complete hydrolysis divided by the number of moles present in the mixture before hydrolysis. For example, for arabinoxylan, the number of moles of monomers can be calculated as the weight of arabinoxylan divided by 132 (molecular mass of xylose and arabinose residues). The number of moles before hydrolysis can be determined by the number of xylose reducing ends as explained in Courtin et al, 2000 (Courtin et al. 2000. J. Chromatography A866, 97-104). For native inulin, or for oligofructose enzymatically synthesized from saccharose, the av $DP_n$ can be calculated by dividing the total amount of glucose and fructose (after hydrolysis) by the total amount of glucose (after hydrolysis) of this inulin. For partially hydrolyzed inulin, the av $DP_n$ can be calculated from the results of high performance anion exchange chromatography with pulsed amperometric detection (HPAEC—PAD or Dionex) analysis.

(2) Examples of suitable methods of analysis for av $DP_w$ determination are described in the literature such as for example in EP1758470 hereby incorporated herein by reference.

As used herein, the term "polysaccharide" refers to a carbohydrate composed of a large number (DP>20) of monosaccharides that are linked by glycosidic linkages. Non-limiting examples of naturally occurring polysaccharides are plant cell wall polysaccharides such as cellulose, pectins, arabinans/arabans, arabinoxylans, xylans, arabinogalactans, xyloglucans, betaglucans or other polysaccharides like starches, galactomannans, mannans, arabinogalactans, and fructans.

As used herein, the term "oligosaccharide" refers to a carbohydrate composed of a limited number of monosaccharides that are linked by glycosidic linkages; the DP generally ranging from 2 to 20. Non-limiting examples of naturally occurring oligosaccharides are saccharose, cellobiose, raffinose, xylo-oligosaccharides, fructo-oligosaccharides, and galacto-oligosaccharides.

As used herein, the term "fermentable fibers" refer to a mixture of non-digestible oligosaccharides and/or non-digestible polysaccharides" i.e. that escape digestion and/or absorption in the upper digestive tract of humans mainly due to the configuration of their osidic bonds. They thus arrive in the large intestine where they can be partially or totally fermented by the endogenous microflora. This fermentation process generates gases and/or short-chain fatty acids like for instance acetate, propionate and butyrate.

As used herein, the term "cereals" refer to cereal plants including but not limited to wheat, oat, rye, barley, sorghum, maize, rice, millet, sorghum, and triticale.

As used herein, the term "prebiotic" refers to a non-digestible food ingredient that beneficially affects the host by selectively stimulating the growth and/or activity of one or a limited number of bacteria in the colon, and thus improves host health. (Gibson & Roberfroid, 1995, *J Nutr* 125, 1401-1412.).

As used herein, the term "prebiotic effect" refers to the selective stimulation of the growth and/or activity of one or a limited number of bacteria in the colon, thus improving host health. An example of a suitable marker for a prebiotic effect is the selective stimulation of Bifidobacteria and/or Lactobacilli. Non-limiting examples of the improvement of the health of an individual include the alleviation of constipation, improving gut health, improving mineral absorption, improving lipid metabolism, and/or improving satiety. In the context of the two latter definitions, "host" has to be understood as a human being or an animal.

The term "host", "individual" or "subject" as used herein includes inter alia a subject, patient, target, host or recipient regardless of whether the individual is a human or non-human animal including avian species. The term "host", "individual" or "subject", therefore, includes a human, non-human primate (e.g. gorilla, marmoset, African Green Monkey), livestock animal (e.g. sheep, cow, pig, horse, donkey, goat), laboratory test animal (e.g. rat, mouse, rabbit, guinea pig, hamster), companion animal (e.g. dog, cat), captive wild animal (e.g. fox, deer, game animals) and avian species including poultry birds (e.g. chickens, ducks, geese, turkeys). The preferred individual, however, is a human. However, insofar as the present invention extends to an animal model, the individual may be a mouse, rat, pig, sheep, non-human primate or other non-human animal.

As used herein, the term "food additive" refers to an ingredient, additive, component or supplement suitable for incorporation in human or animal food.

As used herein, the term "functional food additive" refers to an ingredient, additive, component or supplement suitable for incorporation in human or animal food conferring a technical, nutritional and/or health benefit to the host like for example a prebiotic effect and/or another nutritional/health benefit closely related to the selective stimulation of some colonic bacteria such as for the alleviation of constipation, for an improved gut health, for an improved mineral absorption, an improved lipid metabolism, and a better regulation of glycemia/insulinemia, or improved satiety. The "functional food additive" can be added to different types of food comprising but not limited to functional food, dietetic food and food supplements.

As used herein, the term "arabinoxylan" refers to a mixture of polysaccharides and/or oligosaccharides of xylose units linked by beta (1-4) bonds. The xylose units can be substituted to varying extents on O-2 and/or O-3 by arabinose units. Arabinoxylans are thus branched fibers. Ferulic acid, galactose and/or glucuronic acid may also be present in the structure. Arabinoxylan is also classified as a hemicellulose.

In an embodiment, said arabinoxylan may comprise or consist of partial hydrolysis products of arabinoxylan herein referred to as partially hydrolyzed arabinoxylan. As used herein, the terms "partially hydrolyzed arabinoxylan" or "(AXOS)" refer to a mixture of poly- and/or oligosaccharides of xylose units linked by beta (1-4) bonds and substituted to varying extents on O-2 and/or O-3 by arabinose units. Ferulic acid, galactose and/or glucuronic acid may also be present in the structure. The term "partially hydrolyzed arabinoxylan" is meant to have the same meaning as "AXOS". Both terms are used herein interchangeably.

Suitable methods for the preparation of and partial hydrolysis of arabinoxylan to—partially hydrolyzed arabinoxylan comprise, the partial hydrolysis of the arabinoxylan by chemical (for example using acids or alkali agents), enzymatic, physical (heat, pressure) or mechanical (ball milling, wet milling) treatment, before or after starch removal (if applicable), and further purification (removal of most of the proteins, ashes, and other impurities . . . ) by standard techniques known by the person skilled in the art, in order to obtain a product containing at least 50% (calculated as 0.88 multiplied by the sum of arabinose and xylose content after complete acid hydrolysis) of partially hydrolyzed arabinoxylan on dry matter. The end product can be a liquid or a powder. In an embodiment, said arabinoxylan is partially hydrolyzed by endoxylanase under appropriate conditions.

As used herein, the term "degree of substitution" for the arabinoxylan refers to the ratio of arabinose to xylose sub-units in arabinoxylan and/or partially hydrolyzed arabinoxylan. The term "degree of substitution" for the arabinoxylan is used interchangeably with "A/X ratio" or "arabinose/xylose ratio". The A/X ratio can be calculated by measuring, by HPLC, the content of arabinose and xylose in the analyzed sample of arabinoxylan, after complete hydrolysis of the arabinoxylan under hot hydrofluoric acid or sulfuric acid conditions (for example: a 1 M sulfuric acid concentration during 1 hour at 100° C.).

As used herein, the term "inulin" refers to a mixture of oligo- and/or polysaccharides of fructose which may have a terminal glucose. Inulins belong to a class of fibers known as fructans. In an embodiment, Inulin can be represented, depending from the terminal carbohydrate unit, by the general formulae GFn and Fm, wherein G represents a glucose unit, F represents a fructose unit, n is an integer representing the number of fructose units linked to the terminal glucose unit, and m is an integer representing the number of fructose units linked to each other in the carbohydrate chain. Inulins for use in the present invention encompasses inulins with a terminal glucose which are also referred as alpha-D-glucopyranosyk[beta-D-fructofuranosyl](n-1)-D-fructofuranosides, as well as inulins without glucose which are also referred as beta-D-fructopyranosyl-[D-fructofuranosyl]n-1)-D-fructofuranosides. Inulins for use in the present invention can also encompass the hydrolysis products of inulins such as oligofructoses, which are fructose oligomers with a degree of polymerization (DP) of ≤20, and they can also encompass fructose oligomers ending with a terminal glucose with a DP of 3-5 synthesized from saccharose. Suitable oligosaccharide chains of inulin from plant origin for use in the invention can have a degree of polymerization (DP) ranging from 3 to about 100. Inulin can be a liquid or a powder product.

As used herein, the term "short chain fatty acids" or "SOFA" refers a sub-group of fatty acids with aliphatic tails of less than six carbons. They include, but are not limited to acetic acid, propionic acid, isobutyric acid, butyric acid, isovaleric acid, valeric acid, caproic acid, lactic acid and succinic acid.

As used herein, the term "inflammation" refers to the complex biological response of vascular tissues to harmful stimuli, such as pathogens, damaged cells, or irritants. Inflammation can be classified as either acute or chronic. Acute inflammation is the initial response of the body to harmful stimuli and is achieved by the increased movement of plasma and leukocytes from the blood into the injured tissues. A cascade of biochemical events propagates and matures the inflammatory response, involving the local vascular system, the immune system, and various cells within the injured tissue. Prolonged inflammation, known as chronic inflammation, leads to a progressive shift in the type of cells which are present at the site of inflammation and is characterized by simultaneous destruction and healing of the tissue from the inflammatory process. Although the processes involved are identical to local or tissue inflammation, "systemic inflammation" or "SI" is not confined to a particular tissue but involves the endothelium and other organ systems. Systemic inflammation is the result of release of pro-inflammatory cytokines from immune-related cells and the chronic activation of the innate immune system. As used herein the term "systemic" means affecting the entire body. According to the present invention, conditions associated with systemic inflammation are selected from the group comprising insulin resistance; atherosclerosis, ischemic heart disease, strokes; metabolic syndrome; obesity; type-2 diabetes; autoimmune disorders including rheumatoid arthritis and lupus; allergic disorders, including allergic rhinitis, allergic conjunctivitis, asthma, eczema, urticaria, contact dermatitis, systemic allergic response (anaphylaxis); infections like kidney or bladder infections, gall bladder infection, chronic tonsillitis, diverticular disease; acute or chronic infectious or parasitic processes (with exception for intestinal infections or intestinal parasitic processes), including viral, bacterial or fungal, infection; Gram-negative sepsis, endotoxin-induced shock, systemic inflammatory response syndrome (SIRS) or multiple organ dysfunction syndrome. In an embodiment, said systemic inflammation is caused by conditions selected from the group comprising acute or chronic infectious or parasitic processes including viral, bacterial or fungal, infection; Gram-negative sepsis, endotoxin-induced shock. In a preferred embodiment, said systemic inflammation is caused by conditions selected from insulin resistance, obesity, metabolic syndrome and/or type-2 diabetes, preferably obesity.

An example of local inflammation (in opposition with systemic infection) is gastrointestinal inflammation, such as diarrhea, inflammatory bowel disease, Crohn's disease, enterocolitis, ulcerative colitis, allergic colitis, irritable bowel syndrome, pouchitis, post-infection colitis, *Clostridium difficile*-associated diarrhea, Rotavirus-associated diarrhea, or post-infective diarrhea, or diarrheal disease due to an infectious agent, such as *E. coli*.

As used herein, the term "lipopolysaccharide" (LPS) is a component of the gram-negative bacterial cell wall, which can be responsible for initiating a series of highly complex cascading events leading to damage in multiple organs, including liver and lung. LPS can contribute to the initiation and development of inflammation, insulin-resistance and fat storage.

As used herein, the expression "%" refers to "% by weight expressed on dry matter". The % can be calculated on the total composition according to the present invention. Alternatively, the % can be calculated from the ratio between two or more compounds of a mixture.

The present invention relates to a composition comprising inulin and arabinoxylan and its use for preventing, reducing, and/or treating inflammation, for example systemic inflammation. As used herein, the term "comprising" means that the composition contains at least inulin and arabinoxylan. Additional compounds, ingredients, products may or may not be present in such composition. Non limiting examples of additional ingredients include other fermentable fibers, carbohydrates, proteins, fats, minerals, vitamins. In a particular embodiment, the composition of the present invention may also comprise arabinogalactan peptides.

As such, the invention also encompasses a composition consisting of inulin and arabinoxylan and its use for preventing, reducing, and/or treating inflammation, preferably systemic inflammation. Preferably the present composition is used for preventing, reducing, and/or treating systemic inflammation. The present invention therefore also concerns the use of a composition comprising inulin and arabinoxylan for the preparation of a food or a medicament for preventing, reducing, and/or treating inflammation preferably for preventing, reducing and/or treating systemic inflammation. The present invention also concerns a method for preventing, reducing, and/or treating inflammation or systemic inflammation comprising the administration of a physiologically or therapeutically effective amount of a composition comprising inulin and arabinoxylan in an individual in need thereof.

As used herein the term "therapeutically effective amount" of said above-described composition relates to the amount or quantity of said composition required to achieve the desired therapeutic and/or prophylactic effect. Effective amounts may be measured and expressed in g/day.

As used herein the term "physiologically effective amount" of said above-described composition relates to the amount or quantity of said composition required to achieve the desired physiological effect. Effective amounts may be measured and expressed in g/day.

The inventors surprisingly found that inulin and arabinoxylan have synergistic effects in reducing, preventing and/or treating inflammation, in particular systemic inflammation. In a particular embodiment, the present invention provides a composition comprising inulin and arabinoxylan, wherein said inulin and arabinoxylan are present in synergistic amounts. In an embodiment, conditions associated with systemic inflammation are selected from the group comprising acute or chronic infectious or parasitic processes including viral, bacterial or fungal, infection; Gram-negative sepsis, and endotoxin-induced shock. In another embodiment, conditions associated with systemic inflammation are selected from the group comprising insulin resistance, obesity, metabolic syndrome and/or type-2 diabetes. The compositions therefore offer great potential to better resist stress, inflammation and/or immune challenge for animals and humans. In particular, the present inventors have found that a composition comprising inulin and arabinoxylan synergistically attenuate at the same time the elevation of pro-inflammatory cytokines (such as TNF-α, IL1β, IL8, IL12, IFN-γ) and the suppression of anti-inflammatory cytokines (such as IL10, IL4, IL13), following a challenge with LPS. The challenge with LPS can result from certain gram-negative bacteria which are naturally present in the gut or which are introduced at a certain point and cause an infection. Alternatively, the source of LPS may be external, for instance ingestion of contaminated food. Whereas local (i.e. in the gut) or systemic (i.e. in the blood) LPS suppresses anti-inflammatory cytokines and promotes pro-inflammatory cytokines, the present compositions reverse at least partially this situation or prevent at least partially this situation.

As used herein, the term "synergism" or "synergy" refers to two or more agents working together to produce a result not obtainable by any of the agents independently. This term is used to describe a situation where different entities cooperate advantageously for a final outcome. As used herein the terms "synergistic amounts" or "synergetic amounts" refer to amounts of inulin and arabinoxylan which together achieve a more pronounced effect than each alone, or may even achieve an effect greater than for the sum of each alone.

The inventors also found that a composition comprising inulin and arabinoxylan can synergistically reduce the concentration of LPS in the blood and thus can reduce systemic inflammation. Reducing inflammation offers great potential in the fight against, the prevention of, the reduction of and/or the treatment of obesity, metabolic syndrome and/or type-2 diabetes. The invention therefore also relates to a composition comprising inulin and arabinoxylan for the reduction, prevention and/or treatment of obesity, metabolic syndrome and/or type-2 diabetes. The present invention also encompasses a composition comprising inulin and arabinoxylan and/or AXOS for use in preventing, treating and/or attenuating insulin resistance, obesity, metabolic syndrome and/or type-2 diabetes, preferably for preventing, treating and/or attenuating obesity, wherein said arabinoxylan is partially hydrolyzed arabinoxylan and wherein the ratio of said inulin to said arabinoxylan and/or partially hydrolyzed arabinoxylan is between 65%/35% by weight and 90%/10% by weight. The invention also concerns the use of a composition comprising inulin and arabinoxylan for the preparation of a food, a food supplement or a medicament for reducing, treating and/or preventing obesity, metabolic syndrome and/or type-2 diabetes. The invention also encompasses a method for the reduction, prevention and/or treatment of obesity, metabolic syndrome and/or type-2 diabetes comprising the administration of a physiologically or therapeutically effective amount of a composition comprising inulin and arabinoxylan to an individual in need thereof.

The inventors also found that a composition comprising inulin and arabinoxylan, in particular inulin and arabinoxylan in a ratio inulin/arabinoxylan between 65%/35% by weight and 95%/5% by weight, preferably between 65%/35% by weight and 90%/10% by weight, synergistically stimulates the production of short chain fatty acids (SOFA), in particular propionate and butyrate. The inventors also found that a composition comprising inulin and arabinoxylan, in particular inulin and arabinoxylan in a ratio inulin/arabinoxylan between 65%/35% by weight and 95%/5% by weight, preferably between 65%/35% by weight and 90%/10% by weight, synergistically reduces the adipose tissue weight. The present invention therefore also concerns the composition per se and also the use of a composition comprising inulin and arabinoxylan as a food additive, as a functional food additive and/or as a prebiotic.

In an embodiment, the arabinoxylan for use in the present invention can comprise partially hydrolyzed arabinoxylan. The average DP by number of suitable arabinoxylan and/or partially hydrolyzed arabinoxylan for use in the present composition is preferably below 50, for example between 2 and 50, for example between 5 and 50, for example between 2 and 40, for example between 5 and 40, for example between 2 and 30, for example between 5 and 30, for example between 10 and 30, for example between 15 and 30, for example between 20 and 30, for example between 2 and 20, for example between 5 and 20, for example between 5 and 15, for example between 2 and 15. In another embodiment, the average DP by number of suitable arabinoxylan for use in the present composition is preferably between 5 and 40, and even more preferably between 20 and 40.

In an embodiment, the arabinoxylan for use in the present invention contains more than 10% by weight of molecules with a DP>100.

In an particular embodiment, the arabinoxylan and/or partially hydrolyzed arabinoxylan for use in the present composition has an average molecular weight (MW) below 400 kilo Dalton (kDa), for example between 400 Dalton (Da) and 400 kDa, for example between 400 Da and 300 kDa, for example between 400 Da and 200 kDa, for example between 400 Da and 7 kDa, and for example between 400 Da and 4 kDa.

In an particular embodiment, the arabinoxylan and/or partially hydrolyzed arabinoxylan for use in the present composition has an average degree of substitution of at least 0.05, for example 0.06, 0.07, 0.08, 0.09, 0.10, 0.11, 0.12, 0.13, 0.14, 0.15, 0.16, 0.17, 0.18, 0.19, preferably of at least 0.2, for example at least 0.3, for example at least 0.4, for example at least 0.5, for example between 0.5 and 0.9, for example of at least 0.6, for example between 0.1 and 1.2, for example between 0.1 and 0.9, for example between 0.2 and 0.9, for example between 0.2 and 0.5, for example between 0.25 and 0.35.

In an particular embodiment, the inulin for use in the present composition has, an average DP by number below 50, for example between 2 and 50, for example between 2 and 40, for example between 2 and 30, for example between 5 and 30, for example between 5 and 20, for example between 5 and 15, and for example about 10.

In an particular embodiment, the present composition comprises at least 65% of inulin by weight, for example at least 70% by weight, for example at least 80% by weight, for example at least 90% by weight, for example 73% by weight, for example at least 74% by weight, and for example about 75% by weight.

In an particular embodiment, the present composition comprises at least 5% of arabinoxylan and/or partially hydrolyzed arabinoxylan by weight, for example at least 10% of arabinoxylan and/or partially hydrolyzed arabinoxylan by weight, for example at least 15% arabinoxylan and/or partially hydrolyzed arabinoxylan by weight, for example at least 20% arabinoxylan and/or partially hydrolyzed arabinoxylan by weight, for example at least 30% arabinoxylan and/or partially hydrolyzed arabinoxylan by weight, for example about 35% arabinoxylan and/or partially hydrolyzed arabinoxylan by weight, for example at least 23% arabinoxylan and/or partially hydrolyzed arabinoxylan by weight, and for example about 25% arabinoxylan and/or partially hydrolyzed arabinoxylan by weight.

In a further embodiment, the ratio of inulin to arabinoxylan and/or partially hydrolyzed arabinoxylan in the present composition can range between 65%/35% by weight and 90%/10% by weight, for example between 65%/35% by weight and 85%/15% by weight, for example between 70%/30% by weight and 80%/20% by weight, for example between 73%/27% by weight and 77%/23% by weight, for example about 80%/20% by weight, and for example about 75%/25% by weight.

In an embodiment, inulin for use in the composition can originate from or be isolated or obtained from any natural source of inulin known to date, or can be enzymatically synthesized from saccharose, or can be a commercially available inulin. In an embodiment, inulin originates from or is isolated from elecampane, dandelion, dahlia, wild yam, artichoke, Jerusalem artichokes, chicory, jicama, burdock, onion, garlic, agave, yacón, banana, leek, asparagus or camas. In an embodiment, inulin is a (largely) linear fiber. Preferably, inulin originates from, or is isolated from chicory or Jerusalem artichokes. Suitable commercial inulin for use in the invention can be selected from the group comprising Fibruline® Instant, Fibruline® XL, Fibruline® DS, Fibruline® S2, Fibrulose® F97, . . . (Cosucra-Groupe Warcoing, Belgium), Frutafit® IQ, Frutafit® HD, Frutafit® TEX, Frutafit® CLR, Frutafit® L90, Frutafit® L85, . . . (Sensus, the Netherlands), Orafti® ST, Orafti® GR, Orafti® LGI, Orafti® HSI, Orafti® P95, Orafti® L85, Orafti® L60, Orafti® synergyl, Orafti® HP, . . . (Beneo-Orafti, Belgium), Actilight® 950P, Actilight® 950S, Actilight® 850S, . . . (Syral, France).

In a preferred embodiment, inulin for use in the composition originates from chicory or Jerusalem artichokes and has an average DP between 6 and 25.

In an embodiment, said arabinoxylan and/or partially hydrolyzed arabinoxylan for use in the composition can originate from or be isolated or obtained from any natural source of arabinoxylan or can be commercially available arabinoxylan. In an embodiment, said arabinoxylan and/or partially hydrolyzed arabinoxylan originates from, or is isolated from plants, preferably from cereals, or peas. For example, suitable arabinoxylan and/or partially hydrolyzed arabinoxylan can originate from or can be isolated from wheat, rye, barley, maize, pea or oat, and preferably, said arabinoxylan and/or partially hydrolyzed arabinoxylan originates from or is isolated from wheat. For example, said arabinoxylan and/or partially hydrolyzed arabinoxylan originates from or is isolated from wheat bran. For example, said arabinoxylan and/or partially hydrolyzed arabinoxylan originates from or is isolated from the side stream of a wet starch-gluten separation process. Suitable commercial partially hydrolyzed arabinoxylan products for use in the invention can be for instance Opti'flor® (DF3 SAS, France) and Xylooligo®-95P (Suntory, Japan).

The composition according to the present invention can be useful for providing a technical, nutritional and/or health benefit to an individual in need thereof. Said composition can be used for the selective stimulation of the growth and/or activity of the gastro-intestinal microflora. In a further embodiment, said composition can also be used for the alleviation of constipation, for weight management, gut health, for improving mineral absorption, for improving lipid metabolism and/or for a better regulation of glycemia/insulinemia. The present composition can also be used for the reduction of the risk of heart disease, type-2 diabetes, obesity and/or metabolic syndrome, immunomodulation, cancer prevention, positive impact on hepatic encephalopathy, inflammation reduction. The present composition is also particularly useful for improving satiety.

The composition according to the invention can be supplemented to food, for instance to functional food, dietetic food and/or food supplements, as a food additive, in particular a functional food additive. The present invention also encompasses a method for preparing a food product or beverage or food supplement comprising the steps of: (a) providing a composition according to the present invention, and (b) formulating said composition into a food product, a feed product, a beverage or a supplement.

The present invention also concerns a food product containing the composition according to the present invention, as well as a feed product containing the same composition, a beverage containing the same and a food supplement containing the same.

The composition of the invention may be used as a food additive in the production of a food or beverage, or as a basis for a food supplement. In an embodiment, the food or beverage or supplement comprises between 0.1 and 10 g of the composition according to the present invention per serving of said food or beverage or supplement. The present invention also encompasses, the food or beverage or supplement comprising between 0.1 and 10 g of the composition according to the present invention per serving of said food or beverage or supplement, for use in reducing, preventing and/or treating inflammation. In a preferred embodiment, the food or beverage or supplement comprises between 0.5 and 5 g of the composition according to the present invention per serving of said food or beverage or supplement. In an even more preferred embodiment, the food or beverage or supplement comprises between 1 and 4 g of the composition according to the present invention per serving of said food or beverage or supplement.

For pharmaceutical use, the compositions of the invention may be formulated as a pharmaceutical preparation comprising inulin and arabinoxylan and/or partially hydrolyzed arabinoxylan and at least one pharmaceutically acceptable carrier, diluent or excipient and/or adjuvant, and optionally one or more further pharmaceutically active compounds. Such a formulation may be in a form suitable for oral administration.

In an embodiment, the present composition can optionally be combined with at least one pharmaceutically acceptable carrier for oral administration. When combined with a carrier, the weight percent of the carrier on the total composition can be between 1 and 85%. Typical carriers are food and water. If soluble fiber is used, the combination of an aqueous carrier and the fiber will be a solution. If insoluble fiber is used, the combination of an aqueous carrier and the fiber will be a suspension. The compositions can include an inert diluent or an edible carrier. They may be enclosed in gelatin capsules or compressed into tablets. For the purpose of oral therapeutic administration, the composition can be incorporated with excipients and used in the form of tablets, troches, suppositories or capsules. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents. The composition can be administered as a component of an elixir, suspension, syrup, wafer, chewing gum or the like. A syrup may contain, in addition to the active compounds, sucrose as a sweetening agent and certain preservatives, dyes and colorings and flavors. The composition can also be mixed with other active materials which do not impair the desired action, or with materials that supplement the desired action.

The pharmaceutical preparations are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use.

The present composition will generally be administered in an effective amount, which, upon suitable administration, is sufficient to achieve the desired physiological, therapeutic and/or prophylactic effect in the individual to which it is administered. It is to be further understood that for any particular subject, specific dosage regimens should be adjusted over time according to the individual need and the professional judgment of the person administering or supervising the administration of the compositions, and that the dosage ranges set forth herein are exemplary only and are not intended to limit the scope or practice of the composition.

The invention will now be illustrated by means of the following examples, which do not limit the scope of the invention in any way.

EXAMPLES

Example 1

Effect of a Composition Comprising Inulin and Partially Hydrolyzed Arabinoxylan (AXOS) in a Clinical Intervention Trial 1. Materials and Methods
1.1. Products
Maltodextrins (Glucidex 12DE, Roquette Frères, France) were used as the placebo.

The inulin source used in this trial was Fibruline® Instant (COSUCRA-Groupe Warcoing, Belgium), which is a chicory inulin with a DP ranging from 2 to 60 and an average DP (by number) of about 10. Fibruline® Instant was a powder with a dry matter of 96% and contained, on dry matter, 90% of inulin.

The AXOS source used in this experiment was Opti'flor® (DF3 SAS France) and was obtained from purification of the side stream of a wheat starch producing factory using a three phase decanter for the separation of the two main streams—starch and gluten. This side stream was purified in order to eliminate most of the starch, proteins, minerals, and fats, arabinoxylan was partially hydrolyzed by means of an endoxylanase, and the reaction mixture was concentrated and spray dried. The obtained AXOS sample, a powder, was characterized by a dry matter of 95%, an AXOS content of 80% (calculated as 0.88 multiplied by the sum of arabinose and xylose content after complete acid hydrolysis) on dry matter, an average DP of around 25 (calculated as the DP dividing the surface under the chromatographic high performance size exclusion (HPSEC) molecular mass distribution curve, by a vertical line, in two equal parts) and an A/X ratio of about 0.75. 60% of the molecular weight of the AXOS sample was between 1000 and 40000 Da corresponding to a DP between 7 and about 300.

1.2. Subjects

Sixty healthy volunteers (26 men and 34 women), with an average age of 20+/−2 years old, with a stable weight, and a body mass index (BMI) between 18.5 and 27 kg/m2 (21 on average), participated in the experiment. Exclusion criteria were a serious pathological condition, gastrointestinal, vesicular or pancreatic diseases, antibiotic or laxative treatment during the last 6 months before the study, chirurgical intestinal intervention during the last 12 months preceding the study, intolerance to orange juice, diarrhea constipation or chronic or recurrent abdominal pain, regular intake of medication known to affect gastro-intestinal, pancreatic or vascular function, recent gastroenteritis, diabetes, regular consumption of foods or food supplements enriched in pre- or probiotics during the month preceding the study. Subjects gave written informed consent to the protocol, which was approved by the "Committee of protection of persons Nord-Ouest-IV" in France.

1.3. Experimental Design

A double blind, randomized, parallel, placebo-controlled design was applied. The volunteers were randomly assigned to three groups that were homogenous with regard to age and BMI. After a period of 2 weeks of dietary stabilization, for a period of 4 weeks the volunteers ingested daily two servings of a mixture of 1.5 g inulin, 0.5 g AXOS and 0.5 g maltodextrins (inulin-AXOS mixture group), 2.5 g AXOS (AXOS group) or 2.5 g of maltodextrins (placebo group), dispersed in 125 ml orange juice.

Three-day diet records were performed at the beginning and at the end of the four-week intervention period in order to calculate total calorie intake, and the intake of carbohydrates, fiber, fat and proteins.

1.4. Stool and Blood Collection

Stools and fasting blood samples were collected twice, on the first day of the four-week intervention period, i.e., after 2 weeks of dietary stabilization (V1), and after four weeks of products ingestion (V2). Stool samples were collected in plastic containers, and immediately stored at 4° C., during maximum 12 h before SCFA extraction and the aliquot necessary for s-IgA was stored at −80° C.

Venous blood samples were immediately sampled for cytokines analyses and the rest of the samples were centrifuged and plasma was collected and stored at −80° C.

1.5. Ex Vivo Whole Blood LPS Challenge and Expression of Cytokines 1 ml-aliquots of heparinated blood in beads-containing tubes was incubated with 100 µl of an LPS solution (0.2 ng/µl). These aliquots were incubated during 6 and 24 h at 37° C. with moderate agitation. One duplicate of a placebo group blood sample was incubated without LPS. After 6 or 24 h according to cytokines activation kinetics, 0.5 ml of blood sample was mixed in 1.3 ml RNAlater solution and extracted after 3 days.

RNA extraction was performed by using the Ribopure bloodkit (Applied Biosystems) according to manufacturer's directions. Recombinant DNA was prepared with 1 µg of RNA, using the Quantitect Reverse Transcriptase kit (QIAGEN) according to manufacturer's directions. The expression of cytokines was analyzed, with 200 ng of recombinant DNA, by amplification by RT-PCR Sybr Green® according to manufacturer's (Applied Biosystems) instructions, with gene primers of TNF-alpha, IFN-gamma, IL1-beta, IL-2, IL-4, IL-5, IL-8, IL-10, IL-12 and IL-13. The threshold amplification cycles were normalized for each sample towards GAPDH (housekeeping gene) and the relative expression was expressed as a difference of the expression in a LPS-challenged sample to the expression in a control (placebo) without LPS challenge. These analyses were made using the software program REST-MCS version 2 (Pfaffl et al. 2001. Nucleic acids Research, 29, 2002-2007) and according to the formula:

$$R = (E\ \text{target})^{\Delta Cp target(MEAN\ control - MEAN\ sample)} / (E\ \text{ref})^{\Delta Cp ref(MEAN\ control - MEAN\ sample)}$$

wherein R=Relative expression, E target=cytokine expression, E ref=GAPDH expression, ΔCptarget (MEAN control−MEAN sample)=Amplification difference between control and sample for the cytokine, ΔCpref (MEAN control−MEAN sample)=Amplification difference between control and sample for the GAPDH.

Only for TNF-alpha and IL-10, the expression was measured at V1 and V2. For all the other cytokines, the expression was measured only at V2.

1.6. Biochemical Analyses

Short chain fatty acids (SOFA) concentrations of fecal samples were analyzed after water extraction of fecal samples (2 g in 5 ml deionized water), centrifugation (4500 g, 5 min) and acidification (2M sulfuric acid) of the supernatant to a pH of 2, using gas chromatography (GC; Hewlet Packard 5890-FID). The GC was equipped with a free-fatty acid packed column (FFAP WCOT CP 7614 (SGE analytical science), 25 m×0.53 mm; film thickness 1 µm), and a flame ionization detector. Nitrogen was used as carrier gas with a ΔP of 5 psi. The injector and detector temperature were set at 240 and 280° C., respectively. Concentrations of SOFA were calculated based on standards with known concentrations of the different acids. 4-methyl-2-hydroxy-pentanon was used as an internal standard. SCFAs were expressed as µg/g dry matter of fecal sample.

Fecal secretory IgA concentrations in stool samples taken after 4 weeks of products ingestion were measured with an ELISA kit (sIgA ELISA Kit K8870, Immunodiagnostik) after washing with a buffer according to manufacturer's indications. Values were expressed as µg/ml fecal water.

LPS concentrations in blood samples taken after 4 weeks of products ingestion were measured by the LAL chromogenic endpoint assay HIT302 (Hycult) according to manufacturer's indications, after dilution 1/5 in endotoxin free water and 5 min incubation at 75° C. in order to denature protein before reaction. Values were expressed as EU/ml.

1.7. Data Analysis

Statistical univariate analyses were performed using non parametrical tests such as Mann Whitney or Wilcoxon, or a parametrical t-student test. The Pearson correlation test was used for bivariate analyses.

2. Results and Discussion

The three-day diet records showed that all three study groups were homogenous with regard to macronutrient intake and that those intakes did not differ significantly between the beginning and the end of the four-week intervention period. Total fiber intake, not taking into account the fiber content of the test products, was 12.21+/−3.18 g/day for the placebo group, 12.08+/−2.64 for the AXOS group and 11.60+/−3.44 g/day for the inulin-AXOS mixture group.

Concentrations of fecal SCFA were affected by the different treatments (FIG. 1A). AXOS induced a reduction of acetate concentrations (p=0.01) associated with an increase in butyrate concentrations (p<0.001) whereas the inulin-AXOS mixture significantly (p<0.001) increased both propionate and butyrate concentrations, as compared to the placebo treatment. Total SCFA were 15% higher (p=0.028) for the inulin-AXOS mixture group than for the placebo group. For both the AXOS and the inulin-AXOS mixture group, the SCFA profile was shifted towards lower proportions of acetate and higher proportions of propionate and especially butyrate as compared to the placebo group.

Figure 1B:
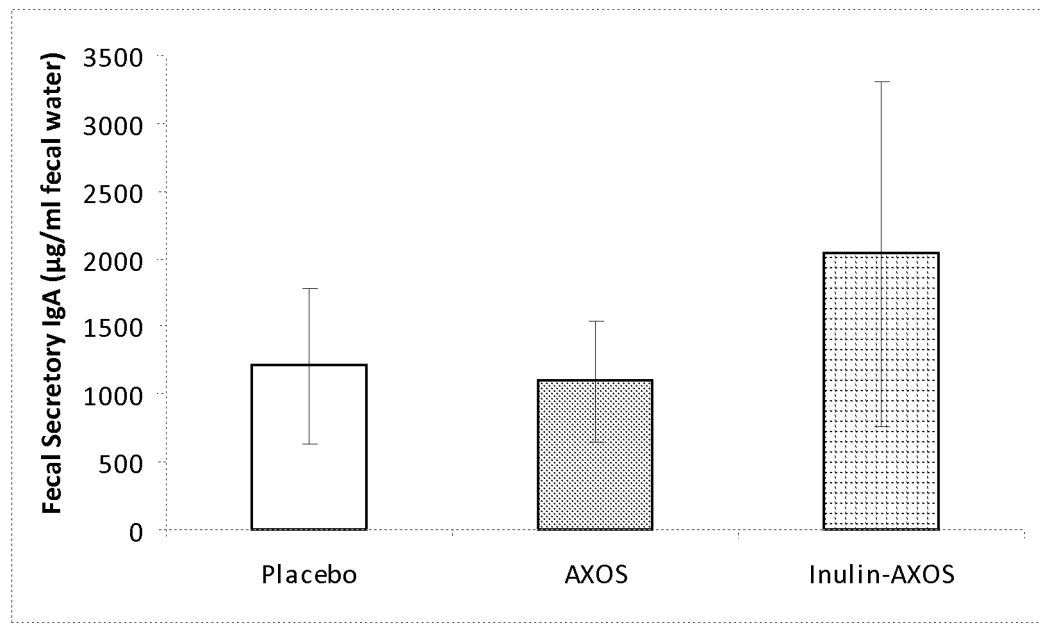

After four weeks of products ingestion, fecal secretory IgA levels were stable for the AXOS group and almost 70% higher for the inulin-AXOS mixture group than for the placebo group (FIG. 1B). Fecal secretory IgA are immunoglobulins secreted by the intestinal mucus layer and these molecules are markers of an improved protection of the colonic mucosa against infectious diseases and opportunistic bacteria.

Figure 1C:
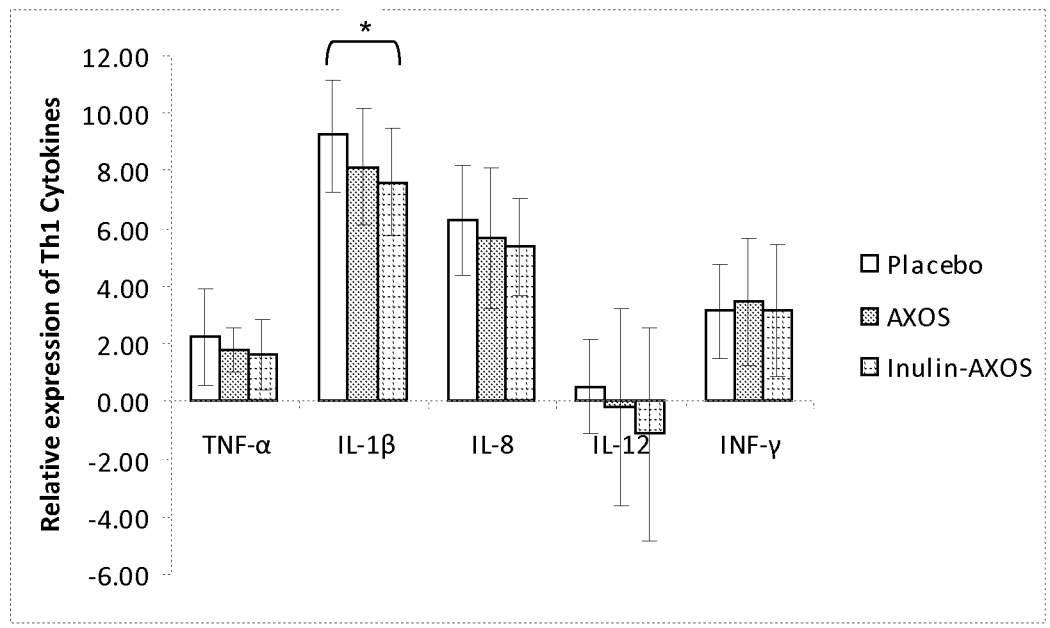
Figure 1D:
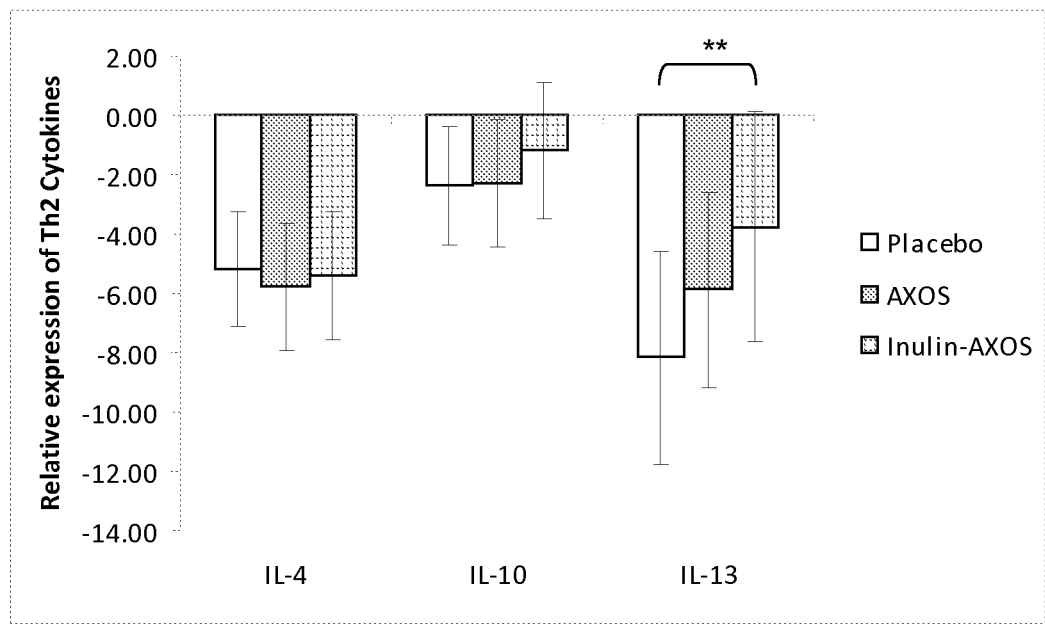

At the end of the four weeks intervention (V2), blood samples were taken and the blood was challenged ex vivo with lipopolysaccharides (LPS). Results of relative expression, of pro-inflammatory cytokines (TNF-alpha, IL1-beta, IL-8, IL-12, IFN-gamma) and anti-inflammatory cytokines (IL-10, IL-4, IL-13) are shown in FIGS. 1C and 1D. These results showed that as compared to the placebo group, the stimulation of pro-inflammatory cytokines by LPS had a tendency to be attenuated for the AXOS group and even more for the inulin-AXOS mixture group. The attenuation of IL1-beta expression reached statistical significance (p=0.045) only for the inulin-AXOS mixture group. Furthermore, the relative expression of TNF-alpha was significantly reduced by 50% (p=0.014) between V1 and V2 in the inulin-AXOS mixture group, which was not the case for the control (results not shown). On the other hand, the suppression of anti-inflammatory cytokines by LPS was also attenuated for the fiber groups especially for the inulin-AXOS mixture group. A strongly significant effect (p=0.01) was observed for IL-13 for the inulin-AXOS mixture group. Also, the relative expression of IL-10 was increased by 55% (p=0.064) between V1 and V2 in the inulin-AXOS mixture group, which was not the case for the control and AXOS groups (results not shown). IL-2 and IL-5 were not modulated by LPS challenge (results not shown). The expression of TNF-alpha and IL-10 following an LPS challenge and measured the beginning of the intervention period (V1) showed no significant differences between the three intervention groups at V1 (results not shown). In summary, the presented results indicate that the mixture of inulin and AXOS could counter, at least partially, the inflammatory response following an immune challenge (such as LPS).

Figure 1E:
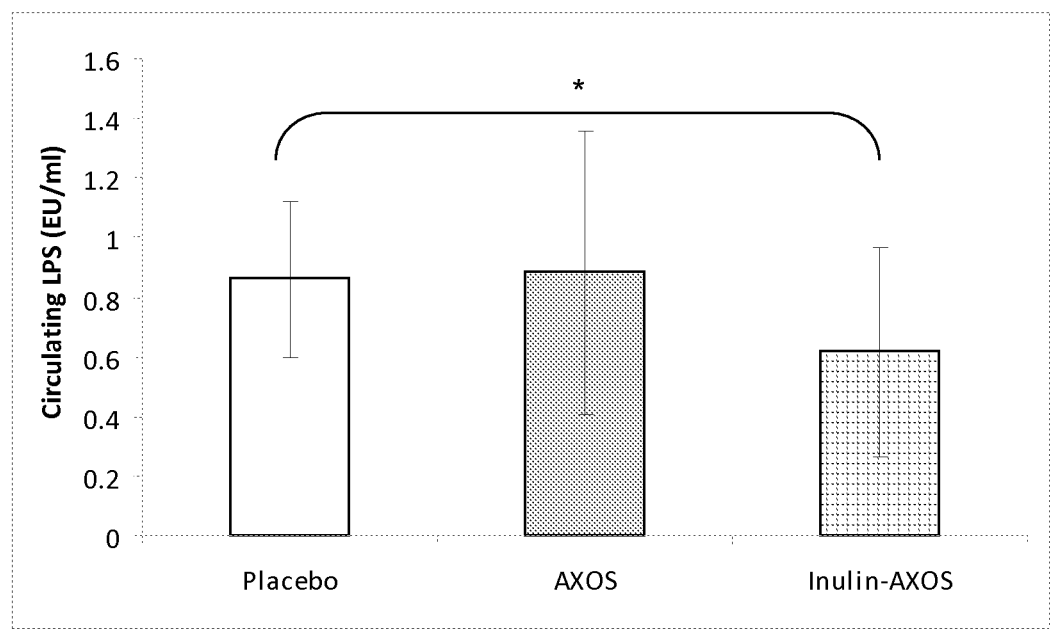
Figure 2A:
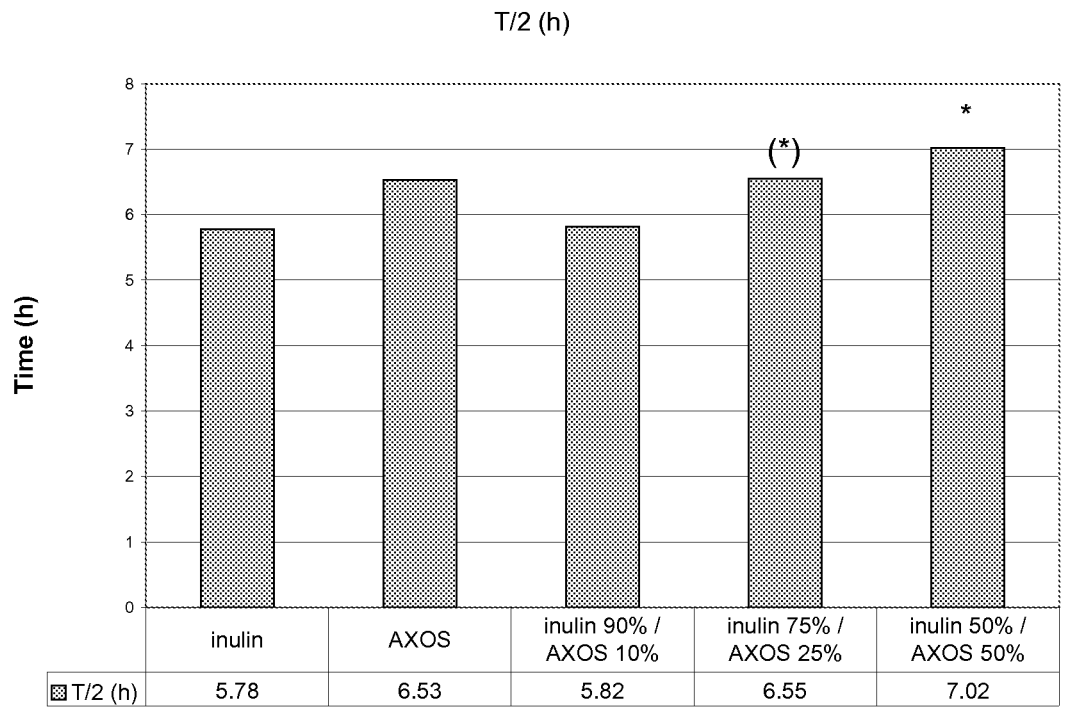
Figure 2B:
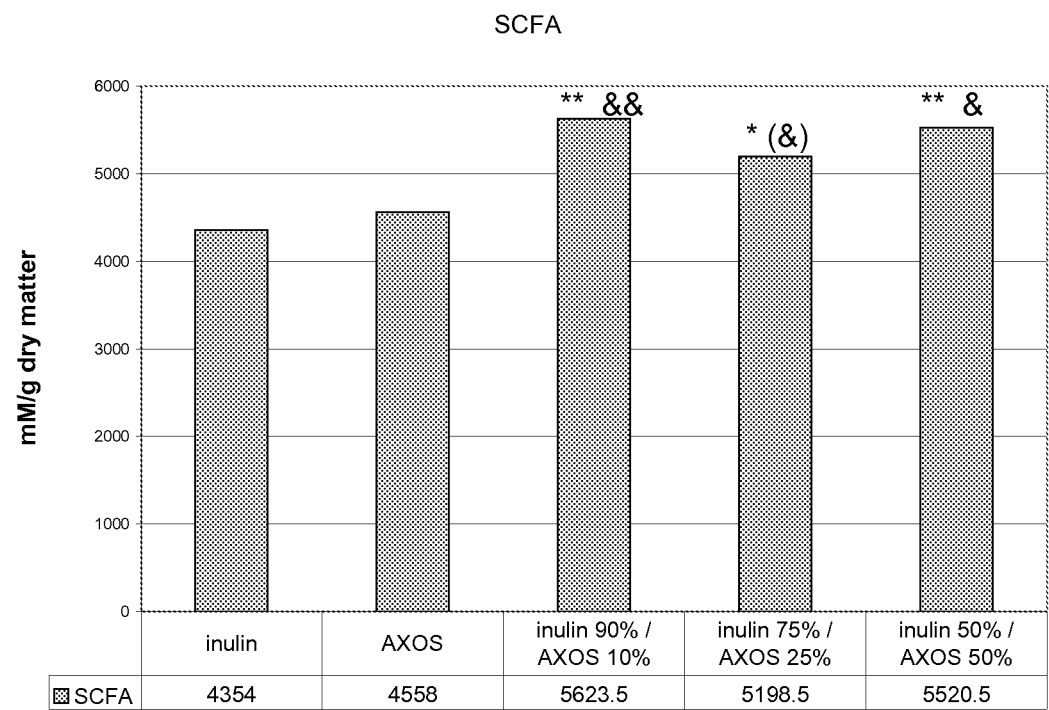
Figure 2C:
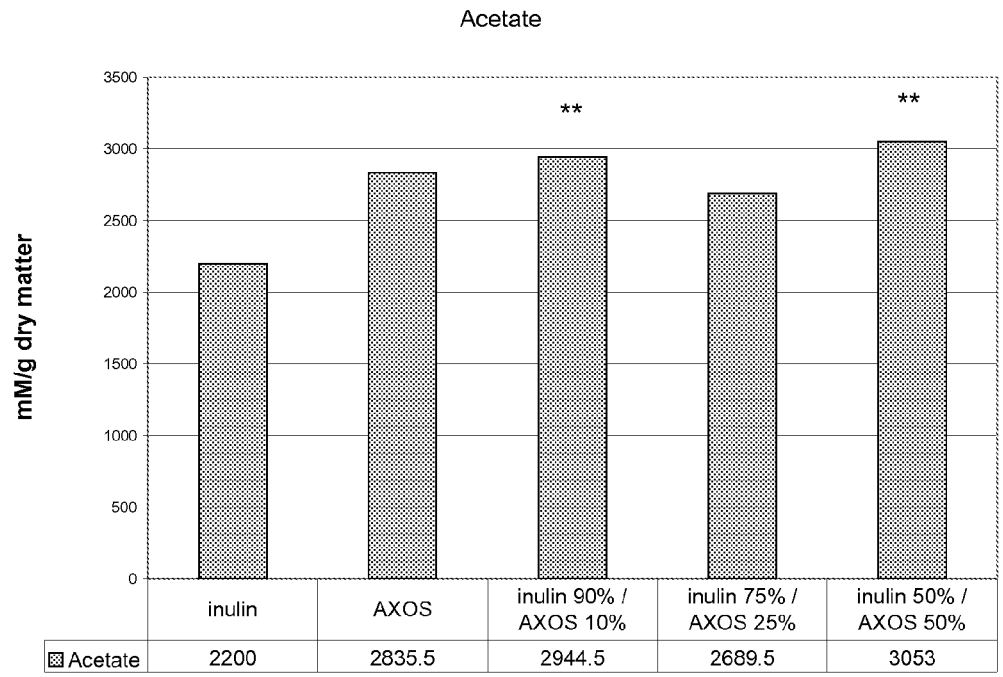
Figure 2D:
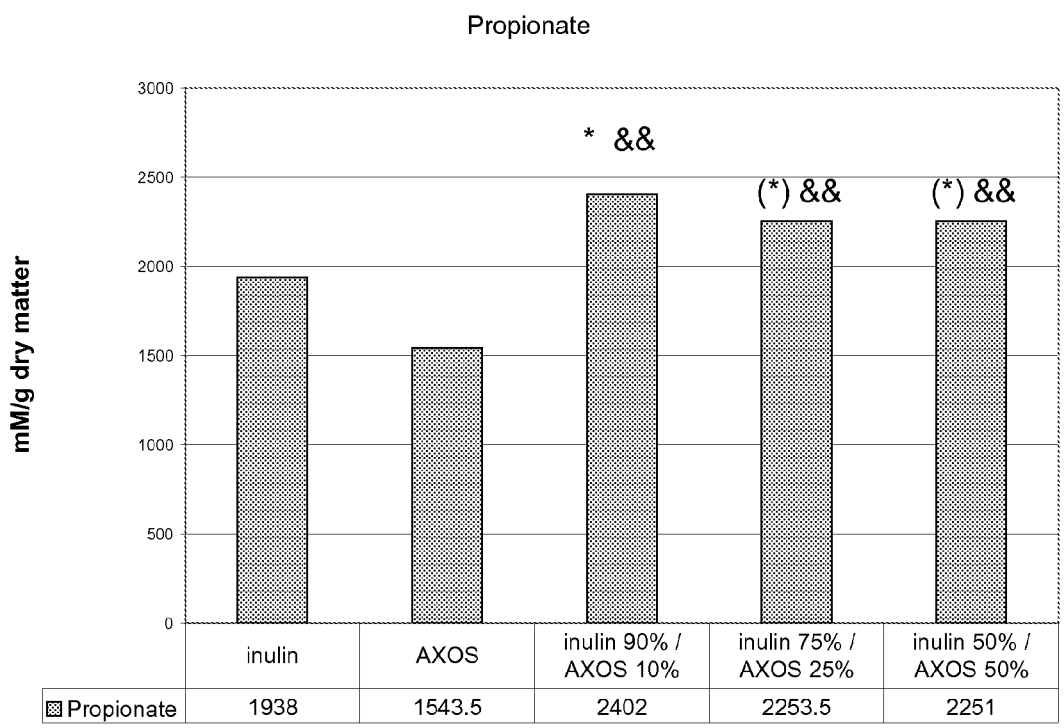
Figure 2E:
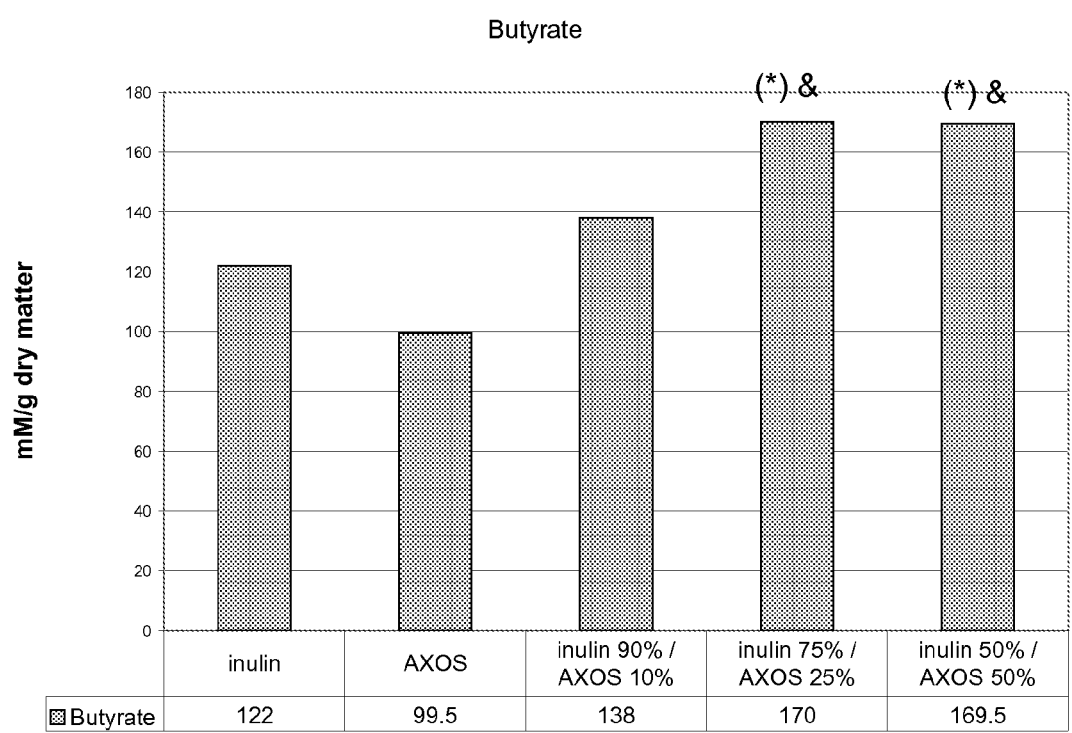

The results also showed (FIG. 1E) that the circulating LPS in the blood samples of the volunteers at the end of the four-week intervention period (before LPS challenge) was 30% lower (p=0.03) for the inulin-AXOS mixture group than for to the placebo group. LPS is a component of the gram-negative bacterial cell wall, which can be responsible for initiating a series of highly complex cascading events leading to damage in multiple organs, including liver and lung. LPS can contribute to the initiation and development of inflammation, insulin-resistance and fat storage. The obtained results thus indicate a significant reduction of the risk of systemic inflammation and endotoxemia for a mixture of inulin and AXOS. This effect was not observed for the AXOS group.

In conclusion, the significantly reduced circulating LPS blood levels together with the modulation of the pro- and anti-inflammatory cytokine balance following an ex-vivo LPS challenge, support the potential of a synergistic mixture comprising inulin and AXOS in reducing, preventing and/or treating inflammation. Corroborating this anti-inflammatory effect of such a mixture are significantly increased fecal butyrate and fecal secretory IgA concentrations.

Example 2

In Vitro Fermentation of Different Mixtures of Inulin and AXOS

1. Materials and Methods
1.1. Products

The inulin source used in this example was Fibruline® Instant (COSUCRA-Groupe Warcoing, Belgium), as characterized in example 1. The AXOS source used in this experiment was Opti'flor® (DF3 SAS, France) and was obtained from purification of the side stream of a wheat starch producing factory using a three phase decanter for the separation of the two main streams—starch and gluten. This side stream was purified in order to eliminate most of the starch, proteins, minerals, and fats, arabinoxylan was partially hydrolyzed by means of an endoxylanase, and the mixture was concentrated and spray dried. The obtained AXOS sample, a powder, was characterized by a dry matter of 96%, an AXOS content of 85% (calculated as 0.88 multiplied by the sum of arabinose and xylose content after complete acid hydrolysis) on dry matter, an average DP of around 37 (calculated as the DP dividing the surface under the chromatographic high performance size exclusion (HPSEC) molecular mass distribution curve, by a vertical line, in two equal parts) and an A/X ratio of about 0.75.

The different test substances were inulin, AXOS, and three mixtures of inulin and AXOS with weight proportions of inulin/AXOS of 90%/10%, 75%/25%, and 50%/50%.

1.2. Animals

A silicone cannula was implanted in the cecum of four Landrace×Piétrain sows with an initial weight of 30 to 35 kg. The animals were individually housed and were fed on average 2 kg of a commercial diet ("Aliment Porc 2 Régal", SCAR, Herve, Belgium) per day. Drinking water was provided ad libitum. The cecal samples collection started after an adaptation period of 3 weeks.

1.3. In Vitro Fermentation

An in vitro model described by Bindelle et al (2007, Animal feed Science and Technology 132, 111-122) was used.

The inoculum used for fermentation was composed of two principal elements: a buffer solution composed of salts and minerals (Menke, K. H., Steingass, H. 1988. Anim. Res. Dev. 28, 7-55) and the cecal contents sampled from the cannulated pigs. The buffer was kept under anaerobic conditions by $CO_2$ bubbling until filling the syringes and the cecal contents were diluted 20 times in the buffer solution. The cecal content was collected by means of a plastic bag attached to the end of the cannula during about 30 minutes. The content was mixed with 150 to 200 ml buffer solution and the mixture was filtered on a metallic filter (250 µm mesh screen) after mechanical pummelling (Stomacher Lab-Blender 400, Seward Medical, Norfolk, UK) of the bags during 60 s.

For each series, three samples of 200 mg of each test substance were placed at the end of a 100 ml Kolbenprober glass syringe. The syringes were than closed and preheated during 24 h in an incubator at 39° C. 30 ml of inoculum was than added to the syringes. The initial volume was read at the moment of placing the syringes in the incubator. For each series, three syringes, only containing inoculum (blanks), were used to quantify the gas production induced by the inoculum in absence of substrate.

1.4. Fermentation Kinetics

The volumes of gas released in the syringes were recorded every hour during the first eight hours of incubation, and after 14, 24, 48, 72 and 96 hours. At each reading, the syringes were re-homogenized by agitation. The volume of gas produced was calculated in function of the initial inoculum in the syringe and the amount of test product added to the syringe. This volume was corrected in function of the quantity of gas produced in the blanks syringes, for each reading. The corrected production of gas is than expressed per g of test substance.

1.5. Short-Chain Fatty Acids (SCFA)

For this experiment, the syringes were prepared as described before. The fermentation of each test substance was stopped at the half-time of asymptotic gas production (T/2), estimated in the preceding step. At T/2, the syringes were put in an ice bath for at least 20 min. The content of each syringe was than collected in a 50 ml falcon tube, the syringes were rinsed with 2 volumes of 50 ml deionized water, and this rinsing water was added to the falcon tube. The mixture was centrifuged at 12000 g during 20 min at 4° C. 5 ml of supernatant of each syringe was removed and cumulated per test substance in a falcon tube of 15 ml. The excess supernatant was discarded. The supernatant and sediment samples were than frozen at −20° C. The analysis and dosage of short-chain fatty acids in the supernatant were performed by HPLC according to Bindelle et al (2007, Animal 18, 1126-1133). The results were expressed as mM/g dry matter of the test substance.

The sediment samples were lyophilized in order to determine the non-degraded dry matter of each test substance for each sample.

1.6. Data Analysis

Gas production was modeled for each syringe according to the mathematical model of France et al (1993. J. Theor. Biol. 163, 99-111). In this way, among others, T/2, expressed in hours, could be calculated.

Statistical analysis of the parameters was performed by means of analysis of variance and a classification of means by the Least Squares Means method using the MIXED procedure of the SAS 8.02 software (SAS Inc., Carry, N.C., USA).

2. Results and Discussion

An in vitro model described by Bindelle et al (2007, Animal feed Science and Technology 132, 111-122) was used to assess in vitro fermentation by pig intestinal contents of inulin, AXOS and different mixtures of inulin and AXOS.

The results are shown in FIGS. 2A to 2E. Inulin and AXOS and the different inulin-AXOS mixtures were all well fermented (FIG. 2A) and generated the production of SOFA. When inulin and AXOS were combined in weight proportions of 90%/10%, 75%125% or 50%/50% respectively, synergistic effects of all three mixtures on the production of SOFA (FIG. 2B), and particularly on propionate (FIG. 2D) and butyrate (FIG. 2E), were obtained.

Example 3

HPSEC Molecular Mass Distribution Profiles of the AXOS Samples Used in Examples 1 and 2

Figure 3A:
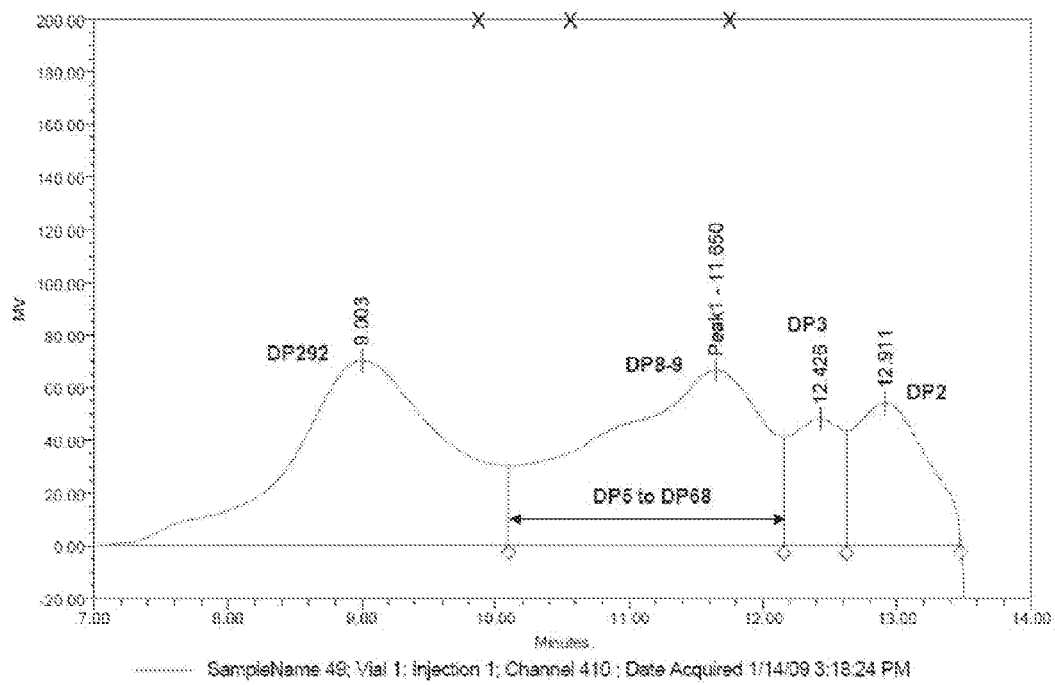
FIGS. 3A and 3B represent HPSEC molecular mass profiles of AXOS samples used in example 1 (FIG. 3A) and example 2 (FIG. 3B). The column was a SUPELCO G-3000. Elution volumes of dextran standards with molecular mass of 1000 Da, 5000 Da and 12000 Da and 50000 Da (this last standard only for FIG. 3B) are indicated by a "X" symbol from right to left.
Figure 3B:
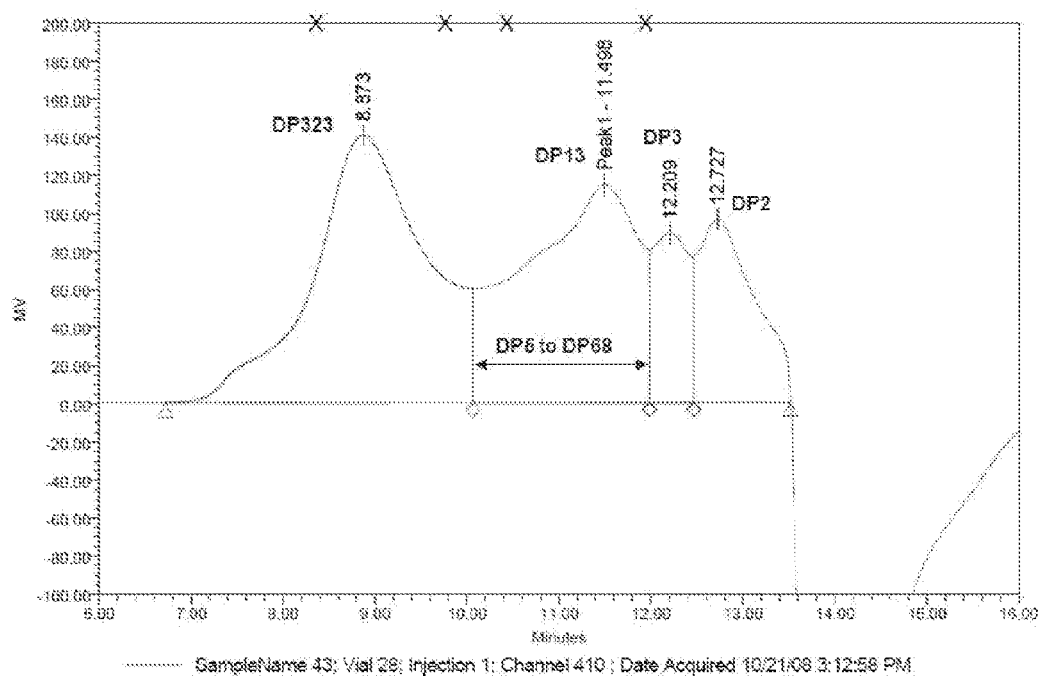

HPSEC was performed on a HPLC system (HPLC Waters 2690 Alliance, Milford, USA) equipped with autoinjection. All preparations were dissolved in distilled water, filtered and injected (100 µl) on a gel-permeation Progel-TSK Supelco G3000 column (Sigma-Aldrich, St. Louis, USA) (300×7.8 mm, separation range: $1\times10^2$–$5\times10^5$ Da). Elution was done with a solution of NaNO3 50 mM and 0.05% NaN3 in distilled water (0.7 ml/min; 30° C.) and monitored with a refractive index detector (Model 2410, Waters Corporation, Milford, USA). Molecular mass markers were dextrans with a molecular mass of 1000 Da, 5000 Da and 12000 Da and 50000 Da (this last standard, only for FIG. 3B) The HPSEC molecular mass distribution profiles of the AXOS samples are shown in FIGS. 3A and 3B.

Example 4

Effect of a Composition Comprising Inulin and Partially Hydrolyzed Arabinoxylan (AXOS) in Rats Suffering from Systemic Inflammation 1. Materials and Methods 1.1. Products The inulin preparation used in this trial was Fibruline® Instant (COSUCRA-Groupe Warcoing, Belgium), which is a chicory inulin with a DP ranging from 2 to 60 and an average DP (by number) of about 10. Fibruline® Instant was a powder with a dry matter of 96% and contained, on dry matter, 90% of inulin.

The AXOS source used in this experiment was obtained from wheat bran. Destarched bran was suspended in demineralised water to obtain a total dry matter of 10%, then adjustment of pH to 6.0 was achieved by sulphuric acid, partial hydrolysis of arabinoxylans was obtained in a thermostatized vessel at 50° C. under continuous stirring during 15 hours after addition of an endoxylanase. Then the enzyme was inactivated by boiling the suspension for 5 minutes. The supernatant containing solubilised material was then separated by filtration and further clarified by centrifugation. Demineralization of the clarified effluent was obtained on a couple of ion exchangers (strong cation-weak anion). After vacuum concentration at pH 4.5, the obtained syrup was dried by lyophilisation. The obtained AXOS preparation (a powder) was characterized by a dry matter of 96%, an AXOS content of 66% (calculated as 0.88 multiplied by the sum of arabinose and xylose content after complete acid hydrolysis) on dry matter, an average DP of around 6 (calculated as the DP dividing the surface under the chromatographic high performance size exclusion (HPSEC) molecular mass distribution curve, by a vertical line, in two equal parts) and an A/X ratio of about 0.38

1.2. Choice of Animal Model and Diet

The ovariectomized rat model was chosen as a model of physiological hormonal deficiency (modeling biological alterations in women linked to menopause) impacting lipid metabolism, oxidative stress, inflammation status and bone health.

In order to further induce metabolic perturbations and systemic inflammation, a western-type pro-inflammatory obesigenic diet was used.

1.3. Animals and Diets

Female rats were randomly allocated to 9 groups of 8 rats and fed one of the semipurified diets. A basic diet was used, as well as a western-type pro-inflammatory obesigenic test diet (Table 1) that had (1) a high lipid content (15%) with a ratio of fatty acids n-6/n-3=35 and 28% saturated fatty acids and with an insufficient content of vitamin E (⅓ of normal needs); (2) 15% saccharose; (3) 18% proteins (casein); and (4) a relative deficiency in minerals (0.5% calcium and 0.05% magnesium). Inulin preparation (7.5%); AXOS preparation (7.5%) or a mixture of inulin preparation (5.625%) and AXOS preparation (1.875%) was substituted for an equal amount of starch in the obesigenic test diet.

TABLE 1 composition of the experimental diets (in %)

| Diet | basic | test | test + AXOS | test + AXOS + inulin | test + inulin |
|---|---|---|---|---|---|
| Casein | 14 | 18 | 18 | 18 | 18 |
| Sucrose | | 15 | 15 | 15 | 15 |
| Alphacel | 5 | 5 | 5 | 5 | 5 |
| Peanut oil | 2 | | | | |
| Lard | | 12 | 12 | 12 | 12 |
| Sunflower oil | | 3 | 3 | 3 | 3 |
| Rapeseed oil | 2 | | | | |
| AXOS preparation | | | 7.5 | 1.875 | |
| Inulin preparation | | | | 5.625 | 7.5 |
| L-cystine | 0.18 | 0.18 | 0.18 | 0.18 | 0.18 |
| Choline bitartrate | 0.25 | 0.25 | 0.25 | 0.25 | 0.25 |
| Mineral Mix (AIN-93) | 3.5 | 3.5 | 3.5 | 3.5 | 3.5 |
| Vitamin mix (AIN-93) | 1 | | | | |
| Vitamin mix (AIN-93 devoided of vitE and vitD/2) | | 1 | 1 | 1 | 1 |
| Starch* | 72.07 | 42.07 | 34.57 | 34.57 | 34.57 |

*Starch was added at the expense of the other components up to 100% of the diet

Rats were either sham-operated (SH) or surgically ovariectomized (OVX), under anesthesia using Imalgen 1000 (Merial, Lyon, France) 0.75 ml/kg body weight, and Vetranquil 1% (Ceva santé animale, Libourne, France) 0.25 ml/kg body weight, administered intraperitoneally. In the sham procedure, the ovaries were exteriorized and replaced to create a stress similar to that obtained with bilateral ovariectomy.

1.4. Experimental Design

The experimental study was conducted on Wistar rats aged 6 months (8 per group) and the experiment continued for 3 months. The animals were housed individually in wire cages in a module maintained at 22° C. and subjected to 12 h-12 h light-dark cycles. They had free access to water and the daily quantity of food distributed was 21 g to prevent overeating consecutive to ovariectomy. The study was conducted in accordance with the regional Ethics Committee (France).

The efficacy of inulin and AXOS, alone or in a combination of 80% inulin/20% AXOS was tested in ovariectomized rats fed a western-type obesigenic diet ("test" diet). These experimental conditions were compared to two more protective conditions: (1) a "basic" diet (rich in micronutriments and with an equilibrated level of macronutrients) and (2) sham-operated animals.

Food consumption (refusals) and weight gain were recorded regularly.

At sacrifice (at the end of the 3 month intervention period), animals fasted for 12 h were anaesthetized by intraperitoneal injection, as previously described. The blood from the abdominal aorta was collected either on gel (clotted activator, Sarstedt) or EDTA tubes and immediately centrifuged (4° C., 5 min, 3500 g). The serum and plasma samples were then frozen at −20° C. until use for different analyses. The subcutaneous and abdominal adipose tissues, as well as the muscles (tibialis anterior and soleus) were removed and weighed.

1.5. Biochemical Analyses

On the animals sacrificed at the end of the study (3 months), serum leptin was analyzed (LINCORIA kit, Millipore SAS, Molsheim, France) and high-sensitivity C-Reactive Protein was assessed in plasma-EDTA on a Konelab20 automat (Thermo Electro Corporation, Vantaa, Finland), using a colorimetric method.

1.6. Statistical Methods

The results are expressed as means±SEM. The significance of differences among treatments was determined by two-way ANOVA analysis (XLSTAT, Addinsoft) followed by a Fisher (LSD) test. Values were considered as significant at $p<0.05$. The Pearson correlation test (parametric) was used in order to analyze possible correlations between parameters.

2. Results and Discussion

As expected, food consumption was significantly lower in sham-operated animals compared to ovariectomized ones ($p<0.0001$). Similarly, sham-operated and ovariectomized animals on high-lipid diets consumed less than those on control diet during the first 10 weeks ($p<0.0001$). The difference was not significant at the end of the study.

Figure 4A:
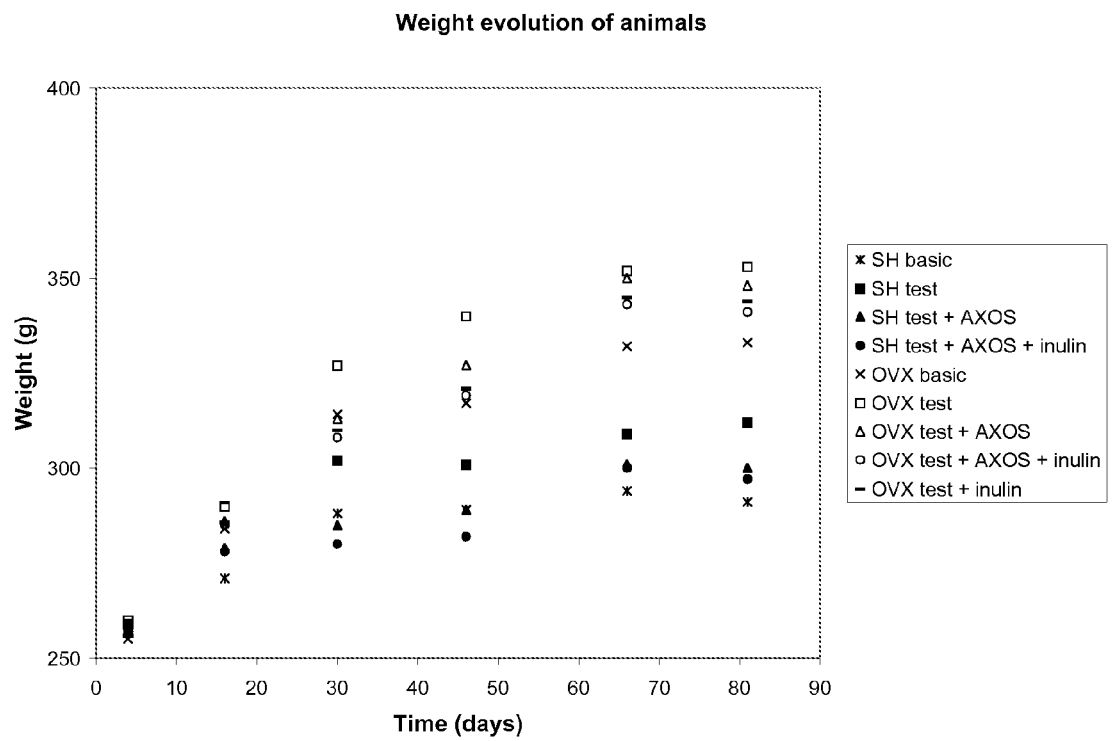
Figure 4B:
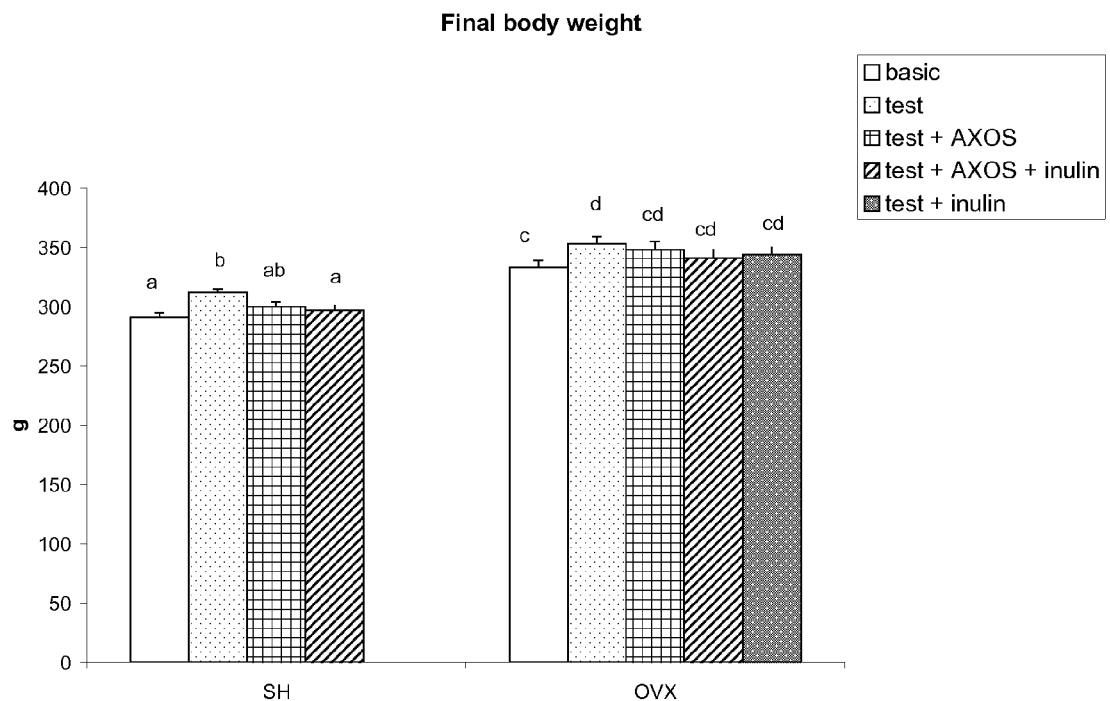

The obesigenic test diet led to higher weight than the basic diet, for both the sham-operated and ovariectomized rats (FIG. 4A). All ovariectomized rats developed higher weight gains than the sham-operated rats, indicating that ovariectomy induces certain metabolic changes. Addition of AXOS and/or inulin to the test diet reduced weight gain in sham and ovariectomized rats. The greatest inhibition of weight gain was obtained with the mixture of inulin and AXOS, although not significant in ovariectomized rats at the end of the study (FIG. 4B).

When analyzing body composition more in detail, more specifically adipose and muscles tissues, differences became even more pronounced, as explained below.

Figure 4C:
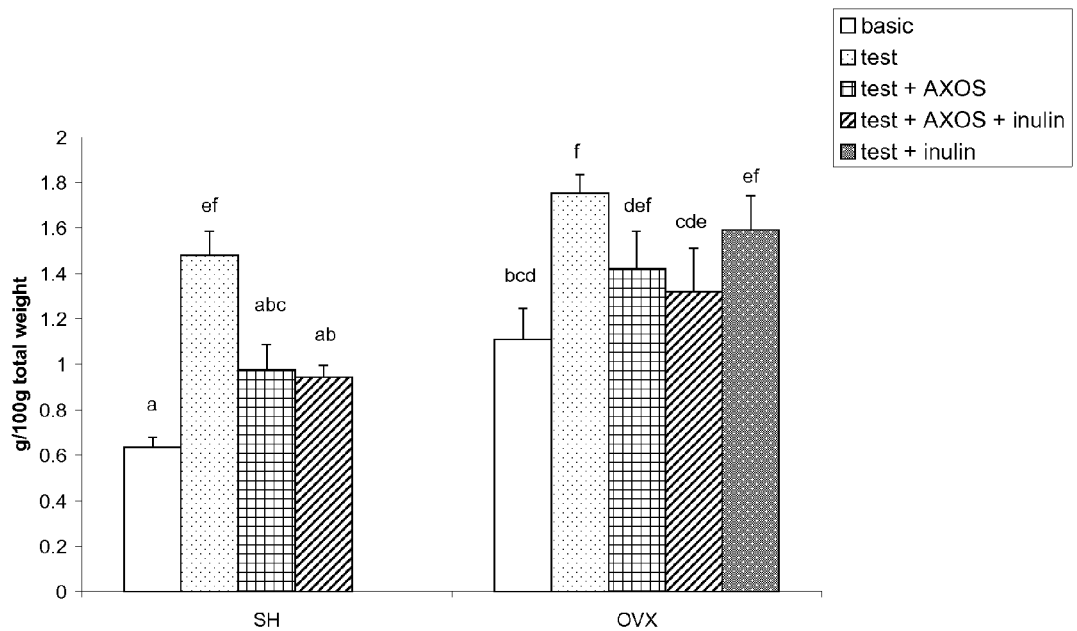
Figure 4D:
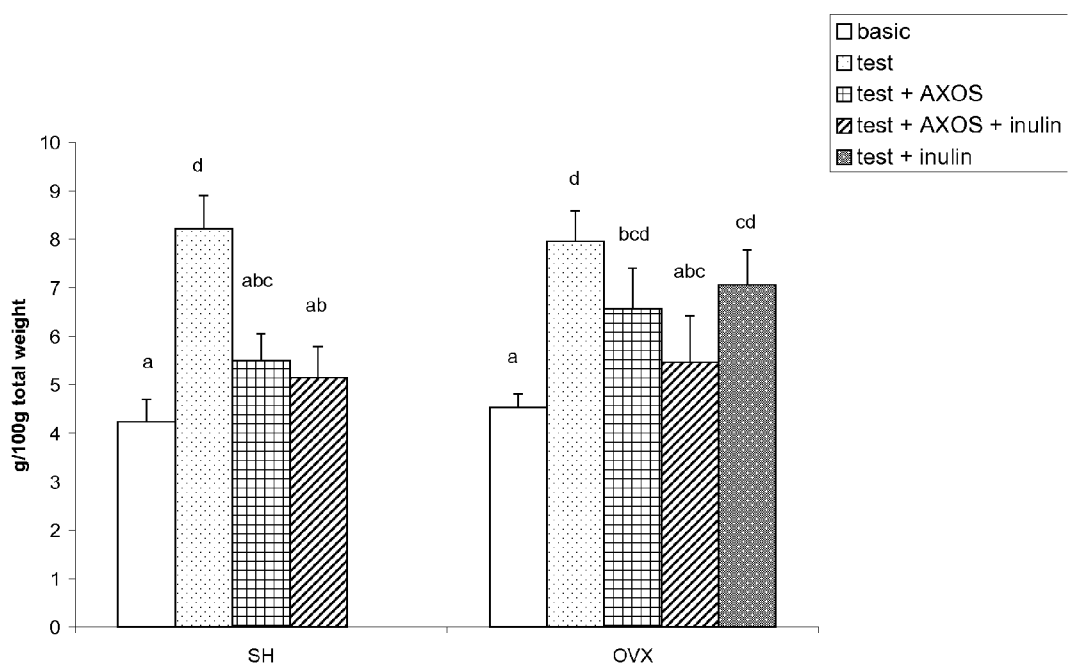

Adipose tissue is an active endocrine organ involved in metabolic syndrome and regulation of inflammation. Two different types of adipose tissue were analyzed: subcutaneous adipose tissue and visceral adipose tissue. As observed for total weight, the obesigenic test diet led to higher subcutaneous and visceral adipose tissue weight than the basic diet, for both the sham-operated and ovariectomized rats (FIGS. 4C and 4D). The ovariectomization in itself significantly increased the subcutaneous adipose tissue but had less impact on the visceral adipose tissue. Addition of inulin and AXOS (alone or in combination) to the test diet reduced subcutaneous and visceral adipose tissue weight in the ovariectomized rats but this reduction became statistically significant only for the mixture of inulin and AXOS, obtaining adipose tissue weights comparable to the basic diet. Also in the sham-operated rats, the fibers added to the test diet significantly reduced the adipose tissue weights.

Figure 4E:
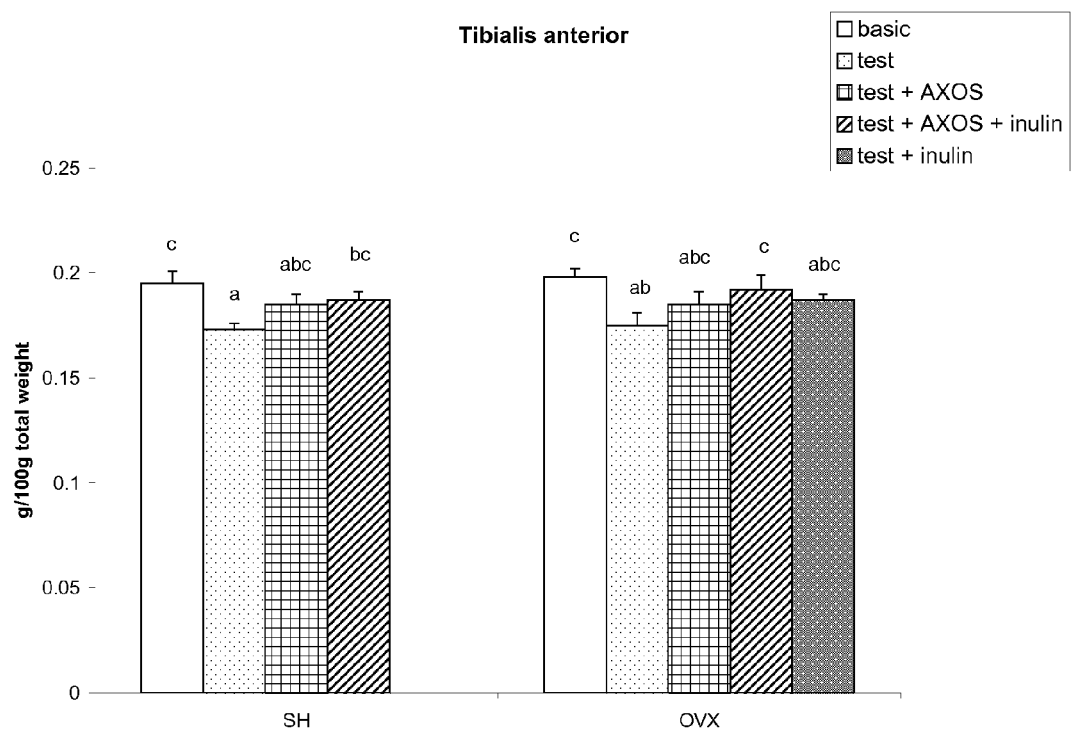
Figure 4F:
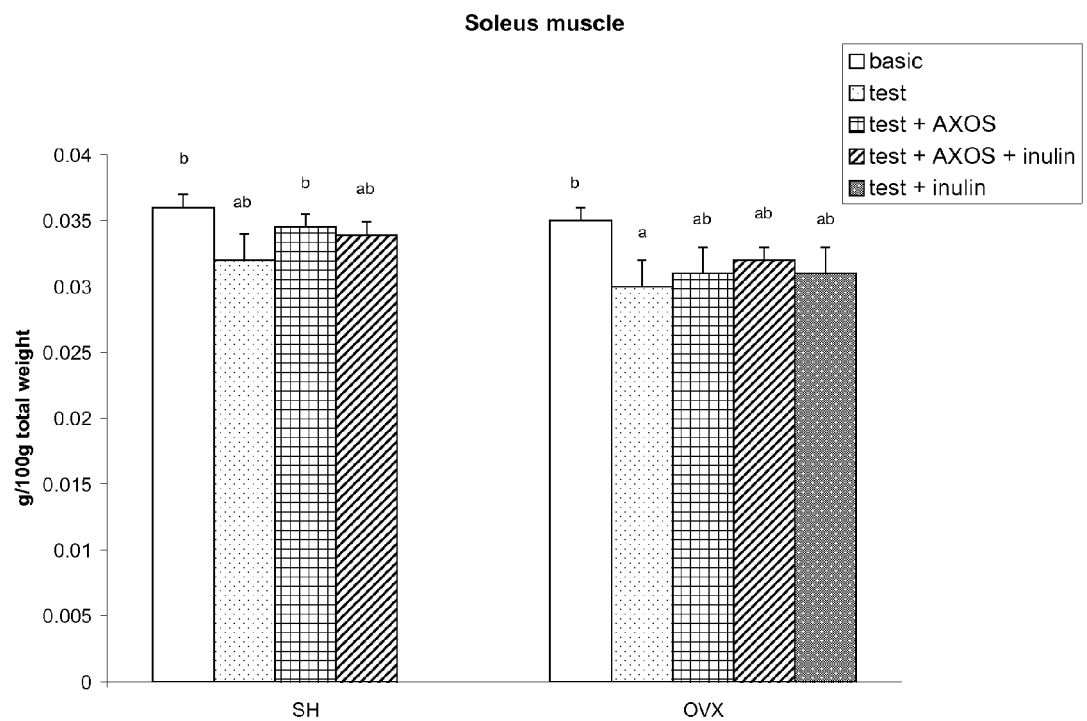

Also two different types of muscle mass were analyzed: tibialis anterior and soleus muscles. Ovariectomization in itself did not greatly impact the tibialis anterior muscle mass, but the obesigenic diet significantly reduced this muscle mass in both sham-operated and ovariectomized rats (FIG. 4E). The addition of inulin or AXOS to the test diet increased tibialis anterior muscle mass as compared to the test diet, however these increases were not statistically significant. Only the inulin-AXOS mixture significantly increased muscle mass as compared to the test diet, both in sham-operated and ovariectomized rats, thereby restoring the muscle mass obtained with the basic more protective diet (FIG. 4E). Similar observations were made for the soleus muscle mass (FIG. 4F), although level of significance was not reached.

The increased adipose tissue weights and the reduced muscle weights as a result of ovariectomization and/or the obesigenic test diet suggest an increased inflammatory status. The observed reduction of adipose tissue weight and concomitant increase of muscle weight for inulin, AXOS and especially the inulin-AXOS mixture could reflect an anti-inflammatory effect of these fibers.

Leptin is a key adipokine involved in regulating food intake and body weight, but in a fasting state would mainly reflect adiposity. The level of leptin analyzed in a fasting state can be considered as a marker of inflammation. Elevated leptin levels in blood circulation are correlated with increased inflammation in obese individuals with cardiovascular complications.

Figure 4G:
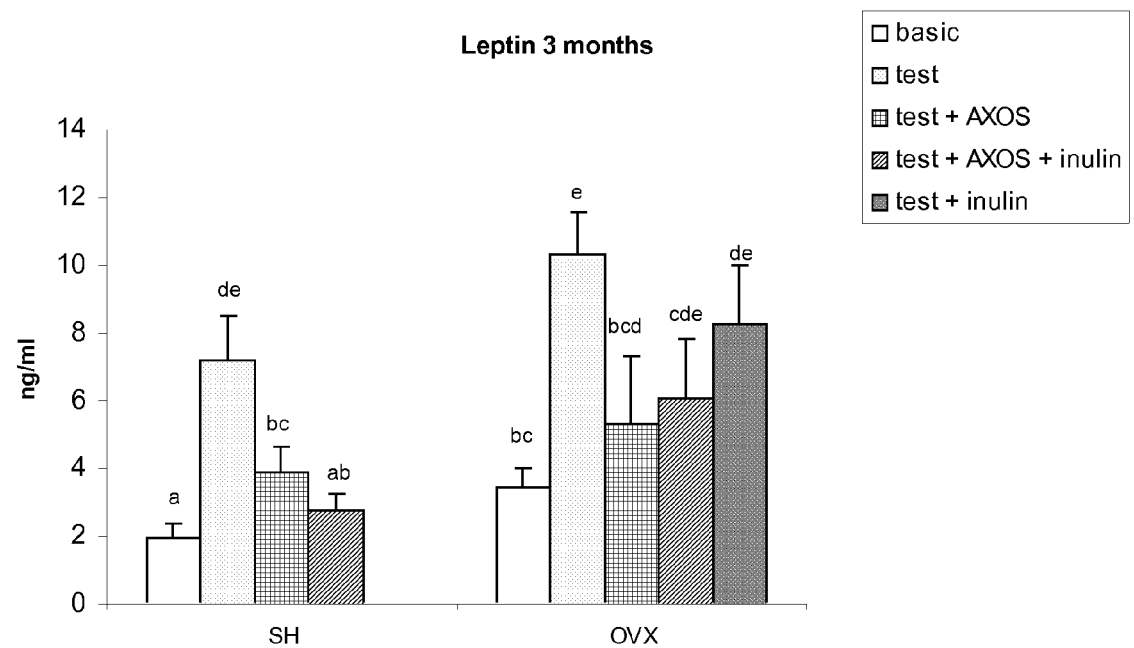

The obesigenic test diet had a huge impact on this parameter, more than doubling the level both in sham-operated and ovariectomized rats (FIG. 4G). Ovariectomy in itself also increased leptin levels. The addition of inulin to the test diet did not impact significantly the leptin level in the ovariectomized rats. The addition of AXOS, and especially the inulin-AXOS mixture, however, significantly reduced leptin levels to the original levels obtained with the basic diet in sham-operated rats. The effect was not significant in ovariectomized rats receiving the inulin-AXOS mixture. Leptin levels were found to be strongly correlated to the visceral adipose tissue weights ($R^2=0.571$; $p<0.0001$ in the Pearson correlation test) corroborating its association with whole body adiposity.

C-reactive protein (CRP) is a marker of inflammation. It is synthesized by the liver. Serum levels of inflammatory markers, in particular high sensitivity (hs)-CRP have been found to be strong predictors of increased risk for type-2 diabetes and cardiovascular disease, independent of other traditional risk factors.

Figure 4H:
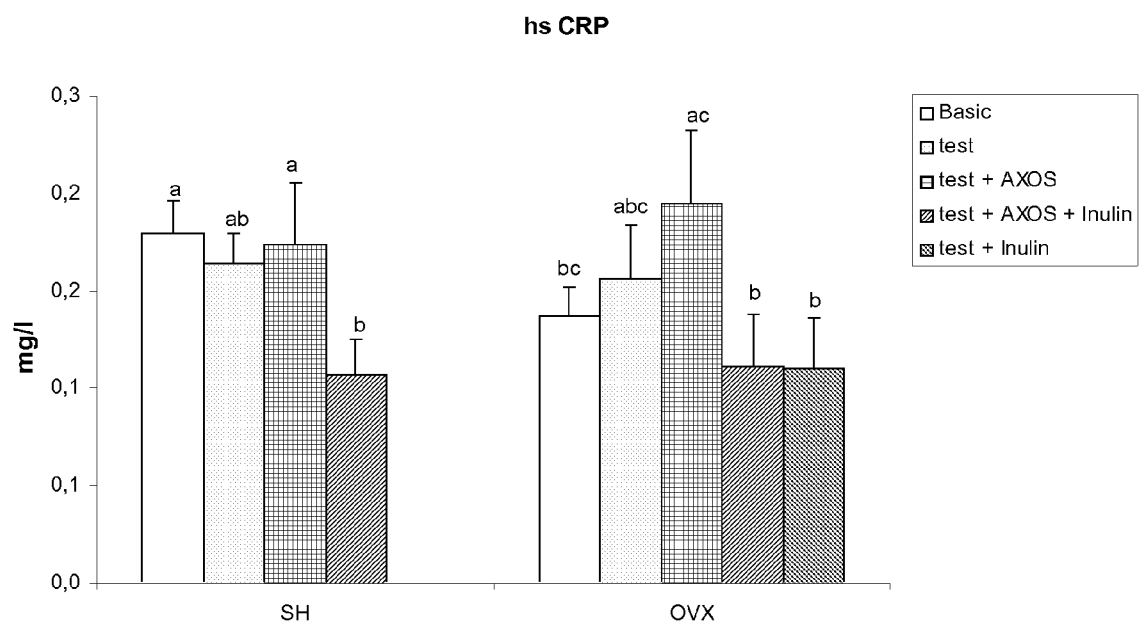

As presented in FIG. 4H, the level of hs-CRP was not greatly affected by ovariectomy nor by the obesigenic diet. The addition of AXOS to the test diet did not modify hs-CRP level in sham and ovariectomized animals. Addition of inulin alone or in combination with AXOS significantly decreased hs-CRP level in both groups suggesting an anti-inflammatory effect of this fiber.

In conclusion, the fermentable fibers used in this experimental setup, inulin and/or AXOS, positively impacted adipose tissue depots and inflammatory status brought about by an obesigenic pro-inflammatory diet and/or a physiological hormonal deficiency inducing inflammation and metabolic perturbations. The mixture of inulin (80%) and AXOS (20%) synergistically reduced sub-cutaneous and visceral adipose tissue weight, with concomitant reduction of leptin and hs-CRP levels, indicating a systemic anti-inflammatory effect of such a mixture.

Example 5

HPAEC-PAD and HPSEC Molecular Mass Distribution Profile of the AXOS Sample Used in Example 4

The high pH anion exchange chromatography with pulse amperometry detection HPAEC-PAD analysis was done on a dionex DX500 line using a CarboPAc PA100 column and a CarboPAc PA100 guard column both kept at 30° C. The flow rate was 1 ml/min. The eluent was NaOH 160 mM. A linear gradient of sodium acetate ranging from 0 to 500 mM was applied during the 90 minutes of the run. Samples were dissolved in water (1 g/l) and filtered on 0.22 µm prior to the injection (25 µL).

Figure 5A:
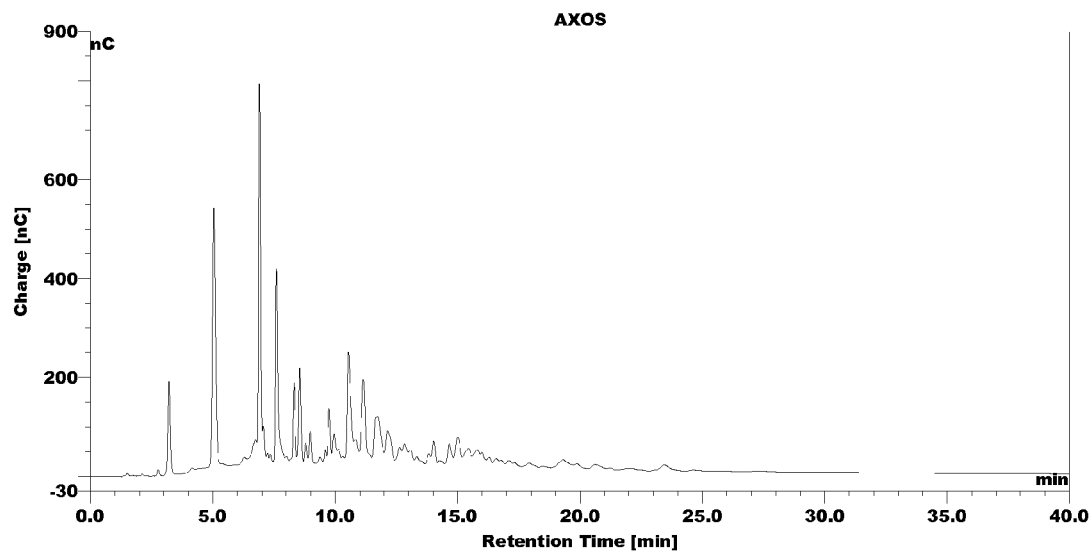
FIG. 5A represents a high pH anion exchange chromatography with pulse amperometry detection (HPAEC-PAD) chromatogram of the AXOS sample used in example 4, performed with a dionex DX500 line using a CarboPAc PA100 column and a CarboPAc PA100 guard column.

The HPAEC-PAD profile shown in FIG. 5A reveals the presence of oligomers. Monomers elute within the 4 first minutes of the run.

Figure 5B:
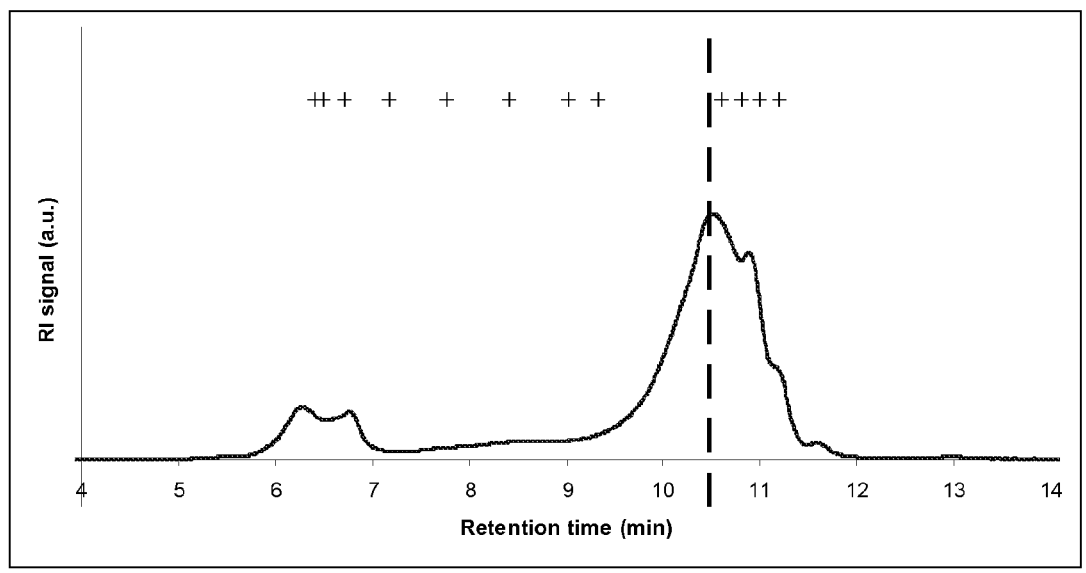
FIG. 5B represents a high performance size exclusion (HPSEC) chromatogram of the AXOS sample used in example 4. The column was a KS-804 size exclusion chromatography column (8.0*300 mm) with a KS-G (6.0*50 mm) guard column. Elution volumes of pullulan standards with molecular mass of 788000, 404000, 212000, 112000, 47300, 22800, 11800 and 5900 Daltons and of stachyose (667 Daltons), maltotriose (504 Daltons), sucrose (342 Daltons) and glucose (180 Daltons) are indicated by a "+" symbol from left to right, thus in decreasing molecular weight order. The dashed line separating the area under the curve in 2 equal parts determines the average Dp~6.

HPSEC (see FIG. 5B) was performed on a Waters HPLC line including a 515 pump, a 717 autosampler and a 2410 refractometer as detector. The separation was done using pure water as mobile phase (1 ml/min) on a KS-804 size exclusion chromatography column (8.0*300 mm) with a KS-G (6.0*50 mm) guard column (SHODEX, SHOWA DENKO EUROPE GmbH Konrad-Zuse-Platz, 4-81829 München/Munich-Deutschland/Germany) both maintained at 70° C. All preparations were dissolved in distilled water, filtered and injected (20 µl). Retention time calibration was done using the P-82 pullulan standard (Shodex) containing the following markers 788000, 404000, 212000, 112000, 47300, 22800, 11800 and 5900 Daltons and with stachyose (667 Daltons), maltotriose (504 Daltons) sucrose (342 Daltons) and glucose (180 Daltons). The corresponding retention times are represented (cross symbols) on the graph from left to right in decreasing molecular weight order (FIG. 5B). The dashed line separating the area under the curve in 2 equal parts determines the average Dp~6.

What is claimed is:

1. A method for reducing or treating inflammation associated with insulin resistance, obesity, metabolic syndrome or type-2 diabetes in a patient, comprising administering a composition comprising inulin and partially hydrolyzed arabinoxylan to the patient, wherein the ratio of said inulin to said partially hydrolyzed arabinoxylan is between 65%/35% by weight and 90%/10% by weight, and wherein the total amount of inulin and partially hydrolyzed arabinoxylan is between 0.1 g and 10 g.

2. The method according to claim 1, wherein said inflammation is systemic inflammation.

3. The method according to claim 1, wherein said inulin has an average degree of polymerization by number below 50.

4. The method according to claim 1, wherein said partially hydrolyzed arabinoxylan has an average degree of polymerization by number below 50.

5. The method according to claim 1, wherein the average molecular weight of said partially hydrolyzed arabinoxylan is between 400 Da to 400 kDa.

6. The method according to claim 1, wherein said partially hydrolyzed arabinoxylan has an average arabinose/xylose ratio of at least 0.05.

7. The method of claim 1, wherein said condition is obesity.

* * * * *